(12) United States Patent
Omenetto et al.

(10) Patent No.: US 12,049,481 B2
(45) Date of Patent: Jul. 30, 2024

(54) OPTICALLY TRANSPARENT SILK HYDROGELS

(71) Applicant: Tufts University, Medford, MA (US)

(72) Inventors: Fiorenzo G. Omenetto, Lexington, MA (US); David L. Kaplan, Concord, MA (US); Benedetto Marelli, Lexington, MA (US); Alexander Nicholas Mitropoulos, Winchester, MA (US)

(73) Assignee: Tufts University, Medford, MA (US)

( * ) Notice: Subject to any disclaimer, the term of this patent is extended or adjusted under 35 U.S.C. 154(b) by 848 days.

(21) Appl. No.: 16/872,679

(22) Filed: May 12, 2020

(65) Prior Publication Data

US 2021/0002335 A1 Jan. 7, 2021

Related U.S. Application Data

(63) Continuation of application No. 16/534,780, filed on Aug. 7, 2019, now abandoned, which is a continuation of application No. 15/025,034, filed as application No. PCT/US2014/057832 on Sep. 26, 2014, now abandoned.

(60) Provisional application No. 61/883,945, filed on Sep. 27, 2013.

(51) Int. Cl.
| | |
|---|---|
| *A61L 27/52* | (2006.01) |
| *A61L 27/22* | (2006.01) |
| *A61L 27/38* | (2006.01) |
| *A61L 27/56* | (2006.01) |
| *B23K 26/361* | (2014.01) |
| *B23K 26/402* | (2014.01) |
| *C07K 14/435* | (2006.01) |
| *C12N 5/00* | (2006.01) |
| *A61K 9/06* | (2006.01) |
| *A61K 47/42* | (2017.01) |
| *B23K 103/00* | (2006.01) |

(52) U.S. Cl.
CPC ...... *C07K 14/43586* (2013.01); *A61L 27/227* (2013.01); *A61L 27/3813* (2013.01); *A61L 27/52* (2013.01); *A61L 27/56* (2013.01); *B23K 26/361* (2015.10); *B23K 26/402* (2013.01); *C12N 5/0068* (2013.01); *A61K 9/06* (2013.01); *A61K 47/42* (2013.01); *A61L 2400/12* (2013.01); *B23K 2103/32* (2018.08); *B23K 2103/38* (2018.08); *B23K 2103/50* (2018.08); *C12N 2533/50* (2013.01); *C12N 2533/90* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 4,233,212 | A | 11/1980 | Otoi |
| 5,245,012 | A | 9/1993 | Lombari |
| 2003/0100108 | A1 | 5/2003 | Altman |
| 2004/0067503 | A1 | 4/2004 | Tan |
| 2011/0014287 | A1 | 1/2011 | Altman |
| 2013/0190222 | A1 | 7/2013 | Kaplan |

FOREIGN PATENT DOCUMENTS

| | | |
|---|---|---|
| CN | 101445546 A | 6/2009 |
| WO | 1997008315 A1 | 3/1997 |
| WO | 2004080346 A2 | 9/2004 |
| WO | 2005012606 A2 | 2/2005 |
| WO | 2005123114 A2 | 12/2005 |
| WO | 2007016524 A2 | 2/2007 |
| WO | 2007112679 A1 | 10/2007 |
| WO | 2008118133 A2 | 10/2008 |
| WO | 2008150861 A1 | 12/2008 |
| WO | 2011041395 A2 | 4/2011 |

OTHER PUBLICATIONS

Altman, G. H. et al., Silk-based biomaterials, Biomaterials, 24:401-416 (2003).
Annabi et al., Tissue Engineering: Part B, 2010, 16: 371-383.
Arai, T. et al., Biodegradation of Bombyx mori Silk Fibroin Fibers and Films, Journal of Applied Polymer Science, 91:2383-2390 (2004).
Berntsson, Svante, Spectrophotometric Determination of Acetone by the Salicylaldehyde Method, Anal. Chem., 28:1337 (1956).
Bini, E. et al., Mapping domain structures in silks from insects and spiders related to protein assembly, Journal of Molecular Biology, 335(1):27-40 (2004).
Cao, Y. and Wang, B., Biodegradation of Silk Biomaterials, Int. J. Mol. Sci., 10:1514-1524 (2009).
Chao, P. et al., Silk hydrogel for cartilage tissue engineering, J. Biomed Mater Res B Appl Biomater., 95(1):84-90 (2010).
Chirila, T., et al., Bombyx mori silk fibroin membranes as potential substrata for epithelial constructs used in the management of ocular surface disorders, Tissue Eng Part A, 14:1203-1211 2008).
Chirila, T., et al., Silk as Substratum for Cell Attachment and Proliferation, Materials Science Forum, 561-565: 1549-1552 (2007).
Choi, M., et al., Light-guiding hydrogels for cell-based sensing and optogenetic synthesis in vivo, Nat. Photonics, 7:987-994 (2013).
Dalby, M. et al., The control of human mesenchymal cell differentiation using nanoscale symmetry and disorder, Nature Materials, 6:997-1003 (2007).
Discher, D.E., et al., Growth Factors, Matrices, and Forces Combine and Control Stem Cells, Science, 324:1673-1677 (2009).
Discher, D.E., et al., Tissue Cells Feel and Respond to the Stiffness of Their Substrate, Science, 310:1139-1143 (2005).

(Continued)

*Primary Examiner* — Ileana Popa
(74) *Attorney, Agent, or Firm* — GTC Law Group PC & Affiliates

(57) ABSTRACT

The present application relates to silk fibroin-based hydrogels, methods for making and using the same.

20 Claims, 24 Drawing Sheets

(56) References Cited

OTHER PUBLICATIONS

Drury, J. and Mooney, D., Hydrogels for tissue engineering: scaffold design variables and applications, Biomaterials, 24:4337-4351 (2003).

Duan, X. and Sheardown, H., Dendrimer crosslinked collagen as a corneal tissue engineering scaffold: Mechanical properties and corneal epithelial cell interactions, Biomaterials, 27:4608-4617 (2006).

Engler, A.J., et al., Matrix Elasticity Directs Stem Cell Lineage Specification, Cell, 126:677-689 (2006).

Fagerholm et al., et al., A Biosynthetic Alternative to Human Donor Tissue for Inducing Corneal Regeneration: 24-Month Follow-Up of a Phase 1 Clinical Study, Science Trans Med., 2:46-61 (2010).

Fagerholm et al., Stable corneal regeneration four years after implantation of a cell-free recombinant human collagen scaffold, Biomaterials, 35:2420-2427 (2014).

Freddi, G., et al., Swelling and dissolution of silk fibroin (Bombyx mori) in N-methyl morpholine N-oxide, Int. J. Biol., Macromol., 24:251-263 (1999).

Gil, E.S., et al., Helicoidal multi-lamellar features of RGD-functionalized silk biomaterials for corneal tissue engineering, Biomaterials, 31:8953-8963 (2010).

Gil, E.S., et al., Response of Human Corneal Fibroblasts on Silk Film Surface Patterns, Macromol. Biosci., 10:664-673 (2010).

Guziewicz, N. et al., Lyophilized Silk Fibroin Hydrogels for the Sustained Local Delivery of Therapeutic Monoclonal Antibodies, Biomaterials, 32(10):2642-2650 (2011).

Higa, K. and Shimazaki, J., Recent Advances in Cultivated Epithelial Transplantation, Cornea, Suppl 1, 27:S41-47 (2008).

Hopkins, A.M., et al., Silk Hydrogels as Soft Substrates for Neural Tissue Engineering, Adv. Funct. Mater., 23: 5140-5149 (2013).

Hu et al., Regulation of Silk Material Structure by Temperature-Controlled Water Vapor Annealina, Biomacraomolecules, 12:1686-1696 (2011).

International Search Report for PCT/US2014/057832, 2 pages (Dec. 11, 2014).

Jin, H.J. and Kaplan, D.L., Mechanism of silk processing in insects and spiders, Nature 424(6952):1057-1061 (2003).

Kikuchi Y., et al. "Structure of the Bombyx mori fibroin light-chain-encoding gene: upstream sequence elements common to the light and heavy chain." Gene 110.2 (1992): 151-158.

Kim, U.J., et al. "Structure and properties of silk hydrogels." Biomacromolecules 5.3 (2004): 786-792.

Lammel, A. et al. "Controlling silk fibroin particle features for drug delivery." Biomaterials 31.16 (2010): 4583-4591.

Lawrence, B.D. et al. "Human corneal limbal epithelial cell response to varying silk film geometric topography in vitro." Acta biomaterialia 8.10 (2012): 3732-3743.

Lawrence, B.D. et al. "Silk film biomaterials for cornea tissue engineering." Biomaterials 30.7 (2009): 1299-1308.

Levis, H.J., et al., Plastic compressed collagen as a biomimetic substrate for human limbal epithelial cell culture, Biomaterials, 31:7726-7737 (2010).

Lucas, F. et al., The Silk Fibroins, Silk Department, Shirley Institute, Manchester, England, 13:107-242 (1958).

Mitropoulos et al., ACS Biomater. Sci. & Eng., 2015, 1: 964-970.

Monti, P. et al., Raman Spectroscopic Studies of Silk Fibroin from Bombyx Mori, Journal of Raman Spectroscopy, 29:297-304 (1998).

Monti, P., et al., Raman spectroscopic characterization of Bombyx mori silk fibroin: Raman spectrum of Silk I, J. Raman Spectosc., 32:103-107 (2001).

Myers, E. and Miller, W., Optimal alignments in linear space, CABIOS, 4(1):11-17 (1988).

Nagarkar, S. et al., Structure and gelation mechanism of silk hydrogels, Physical Chemistry Chemical Physics, 12:3834-3844 (2010).

Omenetto, F. and Kaplan, D., A new route for silk, Nature Photonics, 2:641-643 (2008).

Omenetto, F.G. et al., New Opportunities for an Ancient Material, Science, 329:528-531 (2010).

Peppas, N. et al., Hydrogels in Biology and Medicine: From Molecular Principles to Bionanotechnology, Advanced Materials, 18:1345-1360 (2006).

Preda, R.C., et al., Bioengineered silk proteins to control cell and tissue functions, Methods Mol. Biol., 996:19-41 (2013).

Pritchard, E. et al., Effect of Silk Protein Processing on Drug Delivery from Silk Films, Macromolecular Bioscience, 13:311-320 (2013).

Rockwood, D.N. et al., Materials Fabrication from Bombyx mori Silk Fibroin, Nature Protocols 6(10):1612-1631 (2011).

Sashina, E. et al., Structure and Solubility of Natural Silk Fibroin, Russian Journal of Applied Chemistry, 79 (6):869-876 (2006).

Seib, F.P., et al., pH-Dependent anticancer drug release from silk nanoparticles, Adv Health Mater., 2(12):13 pages (2013).

Shah, A. et al., The Development of a Tissue-Engineered Cornea: Biomaterials and Culture Methods, Pediatr. Res., 63:535-544 (2008).

Takei, F. et al., Further Evidence for Importance of the Subunit Combination of Silk Fibroin in Its Efficient Secretion from the Posterior Silk Gland Cells, The Journal of Cell Biology, 105:175-180 (1987).

Tanaka, K. et al., Determination of the site of disulfide linkage between heavy and light chains of silk fibroin produced by Bombyx mori, Biochimica et Biophysica Acta, 1432:92-103 (1999).

Tanaka, K. et al., Immunological Identification of the Major Disulfide-Linked Light Component of Silk Fibroin, J. Biochem, 114:1-4 (1993).

Tao, H. et al., Silk Materials—A Road to Sustainable High technology, Advanced Materials, 24:2824-2837 (2012).

Wang, X. et al., Silk Nanospheres and Microspheres from Silk/PVA Blend Films for Drug Delivery, Biomaterials, 31(6):1025-1035 (2010).

Wang, Y. et al., In vivo degradation of three-dimensional silk fibroin scaffolds, Biomaterials, 29(24-25): 3415-3428 (2008).

Webster, T.J., et al., Enhanced functions of osteoblasts on nanophase ceramics, Biomaterials, 21:1803-1810 (2000).

Webster, T.J., et al., Osteoblast adhesion on nanophase ceramics, Biomaterials, 20:1221-1227 (1999).

Wray, L. et al., Effect of processing on silk-based biomaterials: Reproducibility and Biocompatibility, Journal of Biomedical Materials Research B: Applied Biomaterials, 998(1):89-101 (2011).

Written Opinion for PCT/US2014/057832, 5 pages (Dec. 11, 2014).

Wu, J., et al., Corneal stromal bioequivalents secreted on patterned silk substrates, Biomaterials, 35:3744-3755 (2014).

Zhang et al., J. Nanoparticle Res., 2007, 9: 885-900.

Zhou, L. et al., Effect of Metallic Ions on Silk Formation in the Mulberry Silkworm, Bombyx mori, J. Phys. Chem. B, 109:16937-16945 (2005).

Zhu, J. and Marchant, RE, Design properties of hydrogel tissue-engineering scaffolds, Expert Rev Med Devices, 8 (5):607-26 (2011).

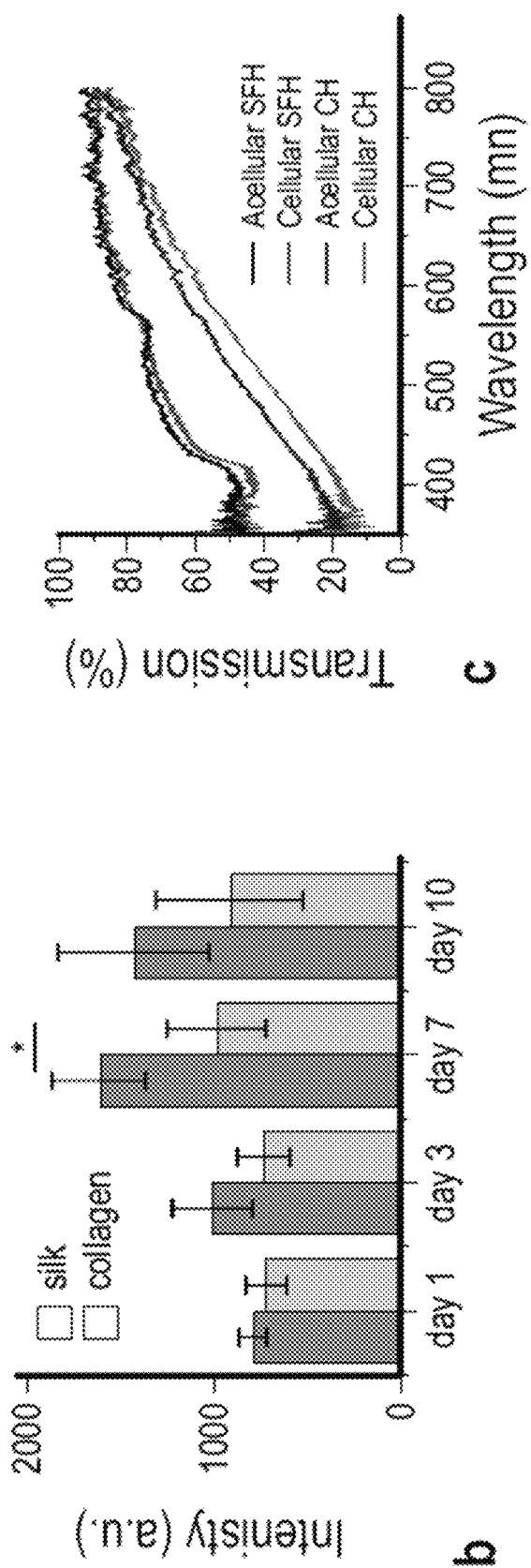
Fig. 10B-C

OPTICALLY TRANSPARENT SILK HYDROGELS

CROSS-REFERENCE TO RELATED APPLICATIONS

The present application is a continuation of U.S. patent application Ser. No. 16/534,780, filed Aug. 7, 2019, which is a continuation of U.S. patent application Ser. No. 15/025,034 filed Mar. 25, 2016, which is a National Stage Patent Application of PCT/US2014/057832 filed Sep. 26, 2014, which claims benefit of U.S. Provisional Patent Application 61/883,945 filed Sep. 27, 2013, the entire contents of each are incorporated herein by reference. The subject matter of the present patent application relates to U.S. Provisional Patent Application 61/909,687 filed Nov. 27, 2013, entitled "LOW MOLECULAR WEIGHT SILK FIBROIN AND USES THEREOF," the entire contents of which are incorporated herein by reference. The subject matter of the present patent application also relates to U.S. Provisional Patent Application 61/883,732 filed Sep. 27, 2013, entitled "LOW MOLECULAR WEIGHT SILK FIBROIN AND USES THEREOF," the entire contents of which are incorporated herein by reference.

GOVERNMENT SUPPORT

This invention was made with government support under grant number EY020856 awarded by the National Institutes of Health. The government has certain rights in the invention.

BACKGROUND

Silk fibroins are produced from silks of various insects, including silkworms. Silk fibroin is typically processed from an aqueous silk solution into varied material formats, such as fibers, foams, particles, films, and/or hydrogels. Silk fibroin processed from aqueous silk solutions have exhibited favorable characteristics, including, for example: desirable mechanical properties, environmental stability, biocompatibility, and tunable degradation. Control over of the molecular weight of the silk and the degree of crystallinity of silk fibroin in the material format towards achieving favorable characteristics have been explored.

SUMMARY OF THE INVENTION

Among other things, the present disclosure provides silk fibroin-based hydrogels. Provided silk fibroin-based hydrogels are characterized by unique features that provide advantages over existing hydrogels. In particular, silk fibroin-based hydrogels as provided herein are optically transparent in the visible spectrum, possess tunable mechanical properties, and/or are non-toxic, so that they are capable of supporting (e.g. with cells). In some embodiments, silk fibroin-based hydrogels as provided are characterized in that they are capable of incorporating functional moieties (e.g. cells) and/or forming desired structures while retaining optical clarity in the visual spectrum. The present disclosure also provides methods of preparing and using such silk fibroin-based hydrogels.

Provided silk fibroin-based hydrogels offer new opportunities at the intersection of biology and technology. Indeed, the possibility of combining optical clarity in the visible spectrum with the well-established, tunable biophysical, biochemical, and biological properties of silk fibroin hydrogels would shine a new light on this material format, enabling the engineering of highly tunable tissue-equivalent constructs with enhanced optical and photonic functionalities. Silk fibroin-based hydrogels as provided herein are therefore particularly suitable as soft biomaterials characterized by physical and mechanical properties that are tunable to match a broad range of human tissues, for example from nerves to cartilage, by mimicking the hydrated nature of the extracellular space.

Implementations of the present disclosure are useful for a wide range of applications, including but not limited to: regenerative medicine, drug delivery, utility for transparent tissues, tissue engineering applications, tissue regeneration, biomedical, biosensing, optogenetics, biomaterials, tunable degradation and/or controlled release applications, optics, photonics, and/or electronics. Provided silk fibroin-based hydrogels can be valuably employed providing a new format of silk fibroin with beneficial attributes, for example, optical, mechanical, and/or structural properties.

In some embodiments, silk fibromin-based hydrogels are or comprise silk fibroin and/or silk fibroin fragments. In some embodiments, silk fibroin and/or silk fibroin fragments of various molecular weights may be used. In some embodiments, silk fibroin and/or silk fibroin fragments of various molecular weights are silk fibroin polypeptides. In some embodiments, silk fibroin polypeptides are "reduced" in size, for instance, smaller than the original or wild type counterpart, may be referred to as "low molecular weight silk fibroin." For more details related to low molecular weight silk fibroins, see: U.S. provisional application concurrently filed herewith, entitled "LOW MOLECULAR WEIGHT SILK FIBROIN AND USES THEREOF," the entire contents of which are incorporated herein by reference.

In some embodiments, for example, silk fibroin-based hydrogels comprise silk fibroin polypeptides having an average molecular weight of between about 3.5 kDa and about 350 kDa. In some embodiments, suitable ranges of silk fibroin fragments include, but are not limited to: silk fibroin polypeptides having an average molecular weight of between about 3.5 kDa and about 200 kDa; silk fibroin polypeptides having an average molecular weight of between about 3.5 kDa and about 150 kDa; silk fibroin polypeptides having an average molecular weight of between about 3.5 kDa and about 120 kDa. In some embodiments, silk fibroin polypeptides have an average molecular weight of: about 3.5 kDa, about 4 kDa, about 4.5 kDa, about 5 kDa, about 6 kDa, about 7 kDa, about 8 kDa, about 9 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 105 kDa, about 110 kDa, about 115 kDa, about 120 kDa, about 125 kDa, about 150 kDa, about 200 kDa, about 250 kDa, about 300 kDa, or about 350 kDa. In some preferred embodiments, silk fibroin polypeptides have an average molecular weight of about 100 kDa.

In some embodiments, silk fibroin-based hydrogels are characterized in that they comprise submicron size or nanosized crystallized spheres and/or particles. In some embodiments, such submicron size or nanosized crystallized spheres and/or particles have average diameters ranging between about 5 nm and 200 nm. In some embodiments, submicron size or nanosized crystallized spheres and/or particles have less than 150 nm average diameter, e.g., less than 145 nm, less than 140 nm, less than 135 nm, less than 130 nm, less than 125 nm, less than 120 nm, less than 115 nm, less than 110 nm, less than 100 nm, less than 90 nm, less than 80 nm, less than 70 nm, less than 60 nm, less than 50 nm, less than 40 nm, less than 30 nm, less than 20 nm, less than 15 nm, less than 10 nm, less than 5 nm, or smaller. In some preferred embodiments, submicron size or nanosized crystallized spheres and/or particles have average diameters of less than 100 nm.

In some embodiments, silk fibroin-based hydrogels are characterized by crystalline structure, for example, comprising beta sheet structure and/or hydrogen bonding. In some embodiments, provided silk fibroin-based hydrogels are characterized by a percent beta sheet structure within the range of about 0% to about 45%.

In some embodiments, silk fibroin-based hydrogels of the present disclosure are characterized by optical transparency in the visible spectrum.

In some embodiments, silk fibroin-based hydrogels exhibit light transmission in a wavelength range between about 400 nm to about 800 nm (i.e. the visible spectrum). In some embodiments, provided silk fibroin-based hydrogels display increase optical clarity when compared with traditional hydrogels, such as collagen based hydrogels. In some embodiments, silk fibroin-based hydrogels are between about 50% and 100% transparent in the visible spectrum. In some embodiments, silk fibroin-based hydrogels are at least 50% transparent in the visible spectrum, at least 55% transparent in the visible spectrum, at least 60% transparent in the visible spectrum, at least 65% transparent in the visible spectrum, at least 70% transparent in the visible spectrum, at least 75% transparent in the visible spectrum, at least 80% transparent in the visible spectrum, at least 85% transparent in the visible spectrum, at least 90% transparent in the visible spectrum, or at least 95% transparent in the visible spectrum.

In some embodiments, silk fibroin-based hydrogels of the present disclosure are characterized by highly tunable mechanical properties. In some embodiments, silk fibroin-based hydrogels of the present disclosure are characterized in that they possess mechanical properties that are tunable to a particular desired range and/or set. In some embodiments, silk fibroin-based hydrogels are engineered so that mechanical, viscoelastic, morphological, structural, and biological properties are tunable.

In some embodiments, mechanical properties, in particular compressive strength, compressive modulus, stress-strain are tunable. In some embodiments, silk fibroin-based hydrogels with tunable properties are characterized in that they exhibit improved structural stability corresponding to increased compressive strength and/or increased compressive modulus.

In some embodiments, a compressive strength of silk fibroin-based hydrogels is tunable. In some embodiments, a compressive strength of silk fibroin-based hydrogels is tunable in a range of between about 0.5 kPa and about 12 kPa without showing an indication of a plastic deformation. In some embodiments, silk fibroin-based hydrogels show a compressive strength of about 0.5 kPa, about 1 kPa, about 1.5 kPa, about 2 kPa, about 2.5 kPa, about 3 kPa, about 3.5 kPa, about 4 kPa, about 4.5 kPa, about 5 kPa, about 5.5 kPa, about 6 kPa, about 7 kPa, about 8 kPa, about 9 kPa, about 10 kPa, about 11 kPa, or about 12 kPa without showing an indication of a plastic deformation.

In some embodiments, a compressive modulus of silk fibroin-based hydrogels is tunable. In some embodiments, a compressive modulus of silk fibroin-based hydrogels is tunable in a range of between about 0.5 kPa and about 20 kPa without showing an indication of a plastic deformation. In some embodiments, silk fibroin-based hydrogels show a compressive modulus of about 0.5 kPa, about 1 kPa, about 2 kPa, about 3 kPa, about 4 kPa, about 5 kPa, about 6 kPa, about 7 kPa, about 8 kPa, about 9 kPa, about 10 kPa, about 11 kPa, about 12 kPa, about 13 kPa, about 14 kPa, about 15 kPa, about 16 kPa, about 17 kPa, about 18 kPa, about 19 kPa or about 20 kPa without showing an indication of a plastic deformation.

In some embodiments, silk fibroin-based hydrogels of the present disclosure may be "tuned" to have elasticity. In some embodiments, provided silk fibroin-based hydrogels therefore possess "tunable elastic properties," which provide flexibility both in structure and downstream applications. In some embodiments, silk fibroin-based hydrogels of the present disclosure are characterized by mechanical properties that are particularly suitable for use in supporting cell growth, function, viability, and/or differentiation. In some embodiments, silk fibroin-based hydrogels are seeded and/or functionalized with live cells.

In some embodiments, silk fibroin-based hydrogels are and/or maintain optically transparency as above provided when seeded and/or functionalized with biologic agents, such as cells.

In some embodiments, silk fibroin-based hydrogels of the present disclosure are characterized in that they are non-toxic. In some embodiments, silk fibroin-based hydrogels are capable of supporting biologic agents, for example, cells and/or functionalized with stabilized heat-labile sensing molecules and/or compounds.

In some embodiments, provided silk fibroin-based hydrogels are configured to allow formation of cell extensions and promote cell/cell and cell/matrix interactions and enhance spreading. In some embodiments, silk fibroin-based hydrogels are seeded and/or functionalized with live cells showed cell viability and cell proliferation over an extended period. In some embodiments, silk fibroin-based hydrogels showed cell viability and cell proliferation for at least 10 days. In some embodiments, silk fibroin-based hydrogels showed cell viability and cell proliferation for at least 15 days. In some embodiments, silk fibroin-based hydrogels showed cell viability and cell proliferation for at least 30 days. In some embodiments, silk fibroin-based hydrogels showed cell viability and cell proliferation for greater than 30 days. To give but one example, in some embodiments, provided silk fibroin-based hydrogels are characterized in that they are capable of supporting living cells, including, for example as evidenced by outgrowth of extensions on human cornea epithelial cells (HCECs).

In some embodiments, silk fibroin-based hydrogels of the present disclosure are characterized by particular degradation properties. In some embodiments, silk fibroin-based hydrogels are degradable.

In some embodiments, silk fibroin-based hydrogels degrade to release an agent useful for treatment of a disease, disorder, or condition.

In some embodiments, silk fibroin-based hydrogels of the present disclosure are characterized in that they may possess a three-dimensional (3D) structure, wherein at least one dimension of the 3D structure is at least 10 μm.

In some embodiments, silk fibroin-based hydrogels are characterized in that they are moldable. In some embodiments, silk fibroin based hydrogels exhibit a capability of being shaped into optical components, for example internally altered by direct laser writing.

In some embodiments, silk fibroin-based hydrogels with a 3D structure comprise a predetermined microstructure fabricated therein and/or thereon. In some embodiments, such predetermined microstructure is a void. In some embodiments, such void may be or comprise a hole, a pore, a channel, a cavity, or combinations thereof.

In some embodiments, silk fibroin-based hydrogels are useful in the formation of optical components. In some embodiments, silk fibroin-based hydrogels are characterized in that they are capable of being shaped and/or molded to form convex or concave geometries that enable the formation of optical components, such as a lens.

In some embodiments, methods of providing, preparing, and/or manufacturing silk fibroin-based hydrogels of the present disclosure comprises providing a silk solution. In some embodiments, a method of providing, preparing, and/or manufacturing silk fibroin-based hydrogels of the present disclosure comprises boiling silk in $Na_2CO$ % for about 10 minutes, about 20 minutes, about 30 minutes, or about 60 minutes. In some embodiments, silk fibers were solubilized in lithium bromide (LiBr) and then dialyzed against water to yield a polymer molecular weight of between about 3.5 kDa and about 350 kDa and a polymer concentration of between about 0.1 mg/mL and about 20 mg/mL.

In some embodiments, methods of providing, preparing, and/or manufacturing a silk fibroin-based hydrogels of the present disclosure comprises adding or mixing a silk fibroin solution with a polar organic solvent, thereby inducing nanogelation. In some embodiments, a polar organic solvent is or comprises, for example, acetone, ethanol, methanol, isopropanol, or combinations thereof. In some preferred embodiments, a polar organic solvent is acetone.

In some preferred embodiments, methods of providing, preparing, and/or manufacturing a silk fibroin-based hydrogels comprises exposing silk fibroin solutions having silk fibroin polypeptides that have an average molecular weight of about 100 kDa and a silk fibroin polypeptide concentration of ≤15 mg/nL to acetone.

In some embodiments, a method of providing, preparing, and/or manufacturing a silk fibroin-based hydrogels of the present disclosure comprises exposing silk fibroin-based hydrogels to a solution of ethylenediaminetetraacetic acid (EDTA). In some embodiments, EDTA is or comprises a crosslinking agent.

In some embodiments, characteristics of silk fibroin-based hydrogels are tuned according to fabrication conditions (e.g., molecular weight of silk fibroin, a concentration of silk fibroin present in solution from which the silk fibroin-based hydogels are prepared, etc.).

In some embodiments, matching, tuning, adjusting, and/or manipulating properties of a silk fibroin-based hydrogel include controlling, for example: by selecting a molecular weight of silk fibroin, by selecting a concentration of a silk fibroin solution, by selecting a solvent for a silk fibroin solution, by exposing silk fibroin-based hydrogels to polyamino carboxylic acids, such as (EDTA) at different concentrations and for different periods (e.g., durations), or by combinations thereof.

In some embodiments, matching, tuning, adjusting, and/or manipulating mechanical properties of a silk fibroin-based hydrogel of the present disclosure is accomplished, at least in part, by selecting a molecular weight of a silk fibroin polypeptide. In some embodiments, a molecular weight of a silk fibroin polypeptide is in a range of molecular weights between about 10 kDa and about 350 kDa.

In some embodiments, matching, tuning, adjusting, and/or manipulating mechanical properties of a silk fibroin-based hydrogel of the present disclosure is accomplished, at least in part, by selecting a polymer solution concentration.

In some embodiments, a polymer solution concentration is in a range of concentrations between about 0.1 mg/mL and about 20 mg/mL.

In some embodiments, matching, tuning, adjusting, and/or manipulating mechanical properties, for example, a compressive modulus and/or a compressive strength of silk fibroin-based hydrogels may be tuned by adding polyamino carboxylic acids, such as (EDTA) at different concentrations and for different periods (e.g., durations).

In some embodiments, matching, tuning, adjusting, and/or manipulating mechanical properties of a silk fibroin-based hydrogel of the present disclosure for use in encapsulating cells is accomplished, at least in part, controlling, for example: by selecting a molecular weight of silk fibroin, by selecting a concentration of a silk fibroin solution, by selecting a solvent for a silk fibroin solution, by exposing silk fibroin-based hydrogels to polyamino carboxylic acids, such as (EDTA) at different concentrations and for different periods (e.g., durations), or by combinations thereof.

In some embodiments, methods of using a silk fibroin-based hydrogel of the present disclosure comprises adhering cells to a surface of a silk fibroin-based hydrogel. In some embodiments, a method of using a silk fibroin-based hydrogel of the present disclosure comprises encapsulating cells within a matrix a silk fibroin-based hydrogel. In some embodiments, a method of using a silk fibroin-based hydrogel of the present disclosure comprises encapsulating cells for introducing cells to a native tissue. In some embodiments, a method of using a silk fibroin-based hydrogel of the present disclosure comprises influencing cell shape.

In some embodiments, methods of providing, preparing, and/or manufacturing a silk fibroin-based hydrogel of the present disclosure for use in encapsulating cells comprises tuning resilience and/or elasticity between a silk fibroin-based hydrogel and a native tissue. In some embodiments, a method of providing, preparing, and/or manufacturing a silk fibroin-based hydrogel of the present disclosure for use in influencing cell shape comprises tuning resilience and/or elasticity between a silk fibroin-based hydrogel and a native tissue.

In some embodiments, a method of providing, preparing, and/or manufacturing a silk fibroin-based hydrogel of the present disclosure comprises controlling a rate of degradation of a silk fibroin-based hydrogel of the present disclosure for maintaining a silk fibroin-based hydrogel shape, optimizing infiltration and/or integration of a silk fibroin-based hydrogel, maximizing cell spreading, and releasing a prescribed amount of an agent or a moiety from a silk fibroin-based hydrogel over a time. In some embodiments, a rate of degradation of a silk fibroin-based hydrogel may be controlled by selecting a molecular weight of a polymer, by selecting a polymer solution concentration, by selecting a specific polymer, by selecting a specific peroxidase, by selecting a specific peroxide, and combinations thereof.

BRIEF DESCRIPTION OF THE DRAWING

The foregoing and other objects, aspects, features, and advantages of the present disclosure will become more apparent and better understood by referring to the following description taken in conjunction with the accompanying figures in which:

FIG. 1(*a*) shows a schematic diagram of the synthesis of silk nanoparticles forming a silk hydrogel. FIG. 1(*a*)(i) shows amorphous silk fibroin molecules. FIG. 1(*a*)(ii) shows beta-sheet formation when amorphous silk fibroin molecules are mixed with acetone. FIG. 1(a)(iii) shows formation of particles with tyrosine residues on the surface. FIG. 1(a)(iv) shows the particle mixture merged together FIG. 1(a.)(v) shows when the acetone is flashed off. FIG. 1(b) shows a macro image of the transparent hydrogel. Scale bar is 1 cm. FIG. 1(c) shows a histogram plot of silk nanoparticle number as a function of particle diameter as measured by dynamic light scattering. FIG. 1(d) shows an SEM image of a dried hydrogel using hexamethyldisilazane. Scale bar is 1 μm.

FIG. 2(a) shows transmission of silk hydrogels with silk boil times of 10 minutes, 30 minutes, and 60 minutes. FIG. 2(b) shows stress-strain curves of silk hydrogels at crosshead rates of 0.102 mm/min, 0.200 mm/min, and 2.000 mm/min for 30 minute boil silk. Each curve represents a hydrogel cross-linked in EDTA for 24 hrs. FIG. 2(c) shows analysis of the compressive modulus of silk hydrogels as a function of time spent in 20 mM EDTA solution for individual crosshead rate.

FIG. 5(a) shows a confocal microscope image of live dermal fibroblasts on the hydrogel surface after 7 days. Scale bar is 375 μm. FIG. 5(b) shows an SEM image of fibroblasts attached on the hydrogel surface. Scale bar is 20 μm.

FIG. 6(a) shows a top view of a converging lens fabricated from a silk hydrogel without fibroblasts on the surface. The focal length of the lens is approximately 1.5 mm. Scale bar is 1 cm, FIG. 6(b) shows a top view of a diverging lens fabricated from a silk hydrogel without fibroblasts on the surface. The focal length of the lens is approximately 1.5 mm. Scale bar is 1 cm.

FIG. 7 shows FIGS. 7A-7D show fabrication of silk fibroin-based hydrogels. FIG. 7(a) shows a schematic representation of the processing steps required to fabricate transparent gels through nanogelation, starting from raw material (silk cocoons). The process starts with silk fibroin purification, which requires boiling the silk cocoons in 0.02 M $Na_2CO_3$, to remove the outer layers of sericin. During cooling, cocoons are unraveled into fibroin fibers. A highly concentrated solution of chaotropic ions (Liar) is used to solubilize the silk fibroin fibers. A dialysis step was then used to remove the chaotropic salts from the solution, yielding a pure fibroin solution. Freestanding silk fibroin-based hydro gels were then formed by mixing silk fibroin solution with acetone. FIG. 7(b) shows a schematic representation of conformational changes within silk fibroin during sol-gel transitions. Silk fibroin in solution possesses an amorphous structure (mostly random coils) and is arranged in micelles. When the silk fibroin solution was exposed to polar solvents, a combination of amorphous-to-crystalline conformational changes together with aggregation results in the formation of silk particles, which arrange together in the presence of water forming a freestanding hydrogel structure. FIG. 7(c) shows an image of a silk fibroin-based hydrogel produced through nanogelation, which enabled the fabrication of a clear material. Scale bar=7.5 mm. FIG. 7(d) shows fabrication of a silk fibroin-based hydrogel through nanogelation in the shape of a meniscus lens. Scale bar=5 mm.

FIG. 8(a) shows light transmission measurements through a 4 mm thick hydrogel showing transparency in the visible spectrum. FIG. 8(b) shows dynamic light scattering measurements of silk fibroin solution (10 mg/ml) (black line) and of the forming silk fibroin gel (red line) were used to evaluate particle size within the two silk fibroin materials. While silk fibroin micelles (solution state) were sharply centered at circa 2 nm, aggregation of silk molecules during sol-gel transition resulted in an increase in the average particle size to 42 nm. The average particle diameter of the forming gels was also found to be dependent on the initial concentration of the silk solution (inset figure). FIG. 8(c) shows SEM micrographs of the silk fibroin-based hydrogel showing a microstructured material, with morphological features of less than 100 nm. FIG. 8(d) shows μRaman spectroscopy of silk fibroin solution and of silk fibroin gels indicating their amorphous (Amide I centered at 1661 cm$^{-1}$ and Amide III centered at 1251 cm$^{-1}$) and crystalline (Amide I centered at 1669 cm$^{-1}$ and Amide III centered at 1235 cm$^{-1}$) structure, respectively.

FIG. 9(a) shows compressive strength of silk fibroin-based hydrogel at crosshead rate of 2.000 mm/min as a function of treatment in 20 mM EDTA solution. Longer EDTA treatment corresponded to an increased compressive strength as a result of the hydrogel crosslinking. FIG. 9(b) shows compressive modulus of silk fibroin-based hydrogels as a function of conditioning time in a 20 mM EDTA solution for different crosshead rates ($*p<0.05$, $p<0.01$, $*p<0.001$). FIG. 9(c) shows representative unconfined compressive stress-strain curves of silk colloidal hydrogels at 0, 1, 2, 7, 19, and 24 hours in 20 mil EDTA solution for crosshead rates of 0.100 mm/min, FIG. 9(d) shows representative unconfined compressive stress-strain curves of silk colloidal hydrogels at 0, 1, 2, 7, 19, and 24 hours in 20 mM EDTA solution for crosshead rates of 0.200 mm/min, and FIG. 9(e) shows representative unconfined compressive stress-strain curves of silk colloidal hydrogels at 0, 1, 2, 7, 19, and 24 hours in 20 mM EDTA solution for crosshead rates of 2.000 mm/min. All the specimens tested were 4 mm thick.

FIGS. 10A-10C show biological characterization of silk fibroin-based hydrogels. Human corneal epithelial cells (HCECs) were cultured on transparent silk fibroin-based hydrogels. Collagen hydrogels were used as controls. FIG. 10(a) shows a confocal microscopy of live/dead assay on HCECs cultured on the surface of silk fibroin and collagen hydrogels at day 1, 3, 7 and 10. Cells were viable and proliferated. Scale bar is 375 μm. FIG. 10(b) shows HCEC metabolic activity as measured by AlamarBlue™ reduction up to day 10($p<0.05$). FIG. 10(c) shows light transmission in acellular and HCECs seeded silk fibroin and collagen hydrogels (SFH and CH, respectively) at day 10. The decrease in light transmission of the silk hydrogel when compared to the results shown in FIG. 8 is associated with loss due to the cell culture media.

FIG. 11(a) shows a transparent silk hydrogel. 11(b) shows an opaque silk hydrogel. 11(c) shows absorbance data comparing a blank, a silk solution, and a silk hydrogel.

FIG. 14(a) shows photographs of silk fibroin-based hydrogels obtained through nanogelation at varying concentrations of silk fibroin solution in a 40 mm wide Petri dish. A concentration dependent increase in light scattering was visible and FIG. 14(b) was quantified through optical transmission measurements. Optical clarity was maintained for silk fibroin concentrations <15 mg/ml. FIG. 14(c) Raman spectra of silk fibroin-based hydrogels at increasing conditioning times in EDTA solution revealed a time dependent blue shift of Amide III beta sheet peak at 1230 $cm^{-1}$ indicating changes in the structural conformation of the silk protein.

FIG. 16(a) shows confocal microscope images using live/dead assay revealed the presence of HDFa at different depths within the hydrogel at day 7 in culture. Subsequent images signify a depth scan at the surface (depth equal to 0 μm), 120 μm from the surface, 240 μm from the surface, and 1000 μm from the surface. Scale bar is 375 μm. FIG. 16(b) shows the maximum intensity projection of HDFa on silk fibroin-based hydrogels at day 7 in culture showed that fibroblasts were well spread on the hydrogel. Scale bar is 375 μm. FIG. 16(c) shows an SEM micrograph of HDFa cultured on silk fibroin-based hydrogel at day 7 showed production of extracellular matrix by cell activity (inset image). Scale bar is 30 μm for the main image and 10 μm for the inset one.

FIG. 17(a) shows maximum intensity projection of HDFa stained with live/dead assay at day 7 in culture and that fibroblast were well spread on the hydrogel. FIG. 17(b) shows maximum intensity projection of HDFa stained with live/dead assay at day 14 in culture and that fibroblast were well spread on the hydrogel. FIG. 17(c) shows maximum intensity projection of HDFa stained with live/dead assay at day 28 in culture and that fibroblast were well spread on the hydrogel. Scale bar is 375 μm. FIG. 17(d) shows an SEM micrograph cellular gel at day 7 collected to investigate cell morphology and production of extracellular matrix. FIG. 17(e) shows an SEM micrograph cellular gel at day 28 collected to investigate cell morphology and production of extracellular matrix. Scale bar is 20 μm. The enlarged micrograph shows close up of extracellular matrix deposition, Scale bar is 2 μm.

DEFINITIONS

Figure 1A:
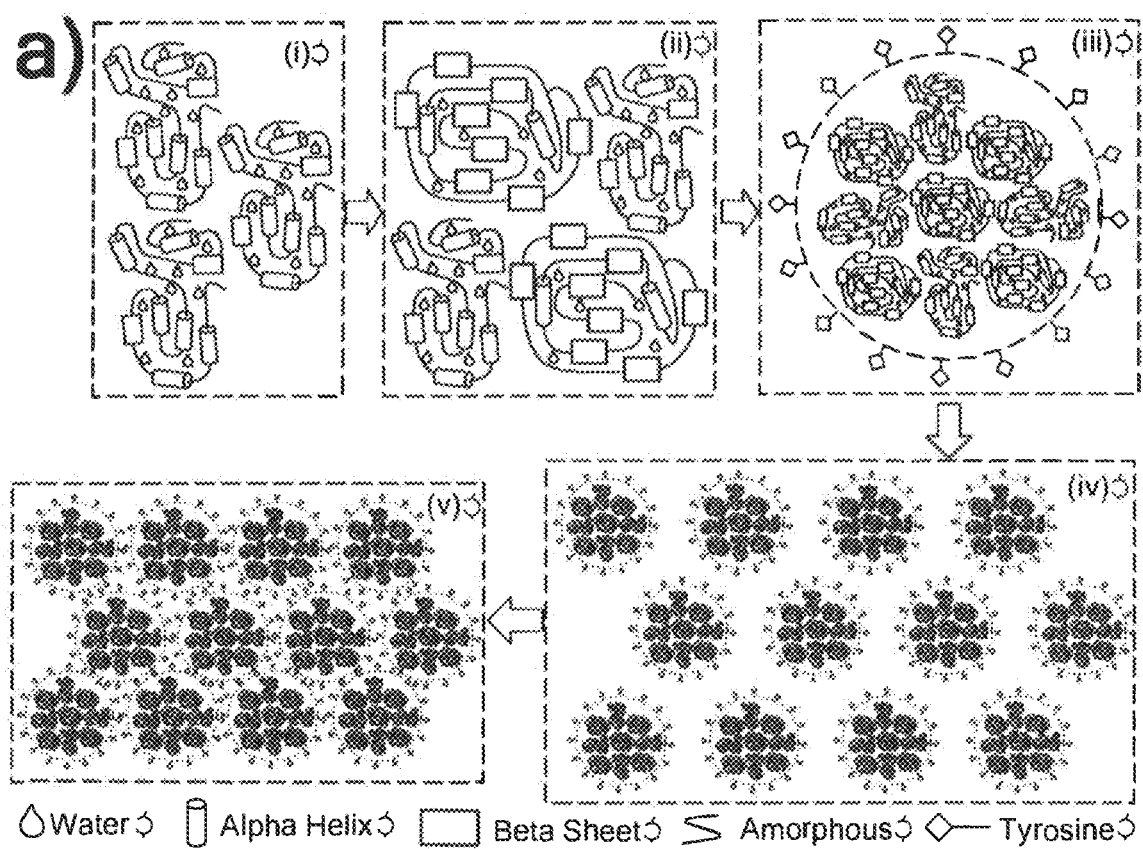
FIGS. 1A-1D show-formation of silk hydrogels.
Figure 1B:
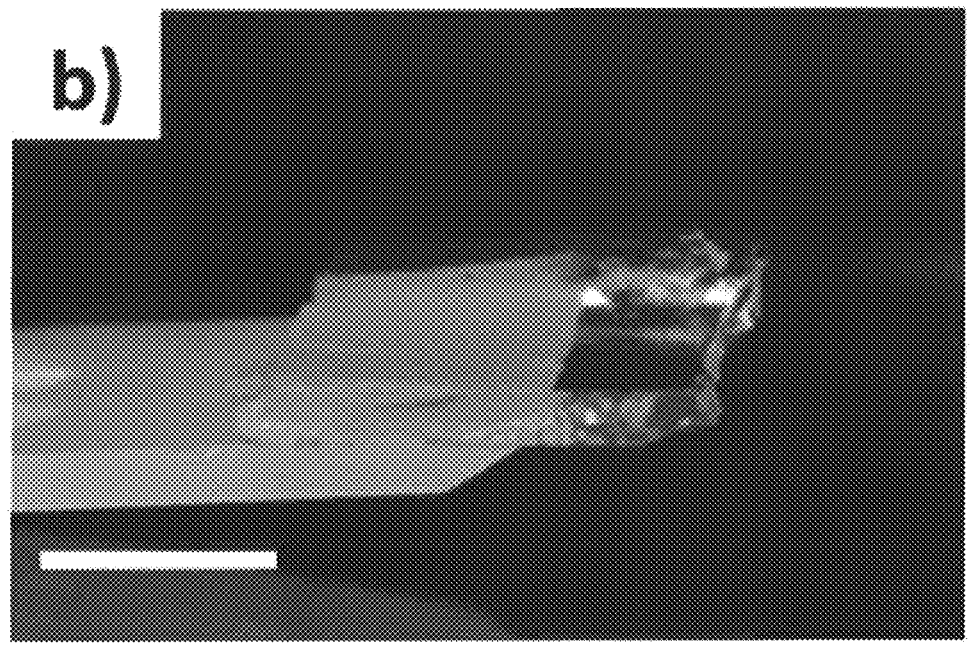
Figure 1C:
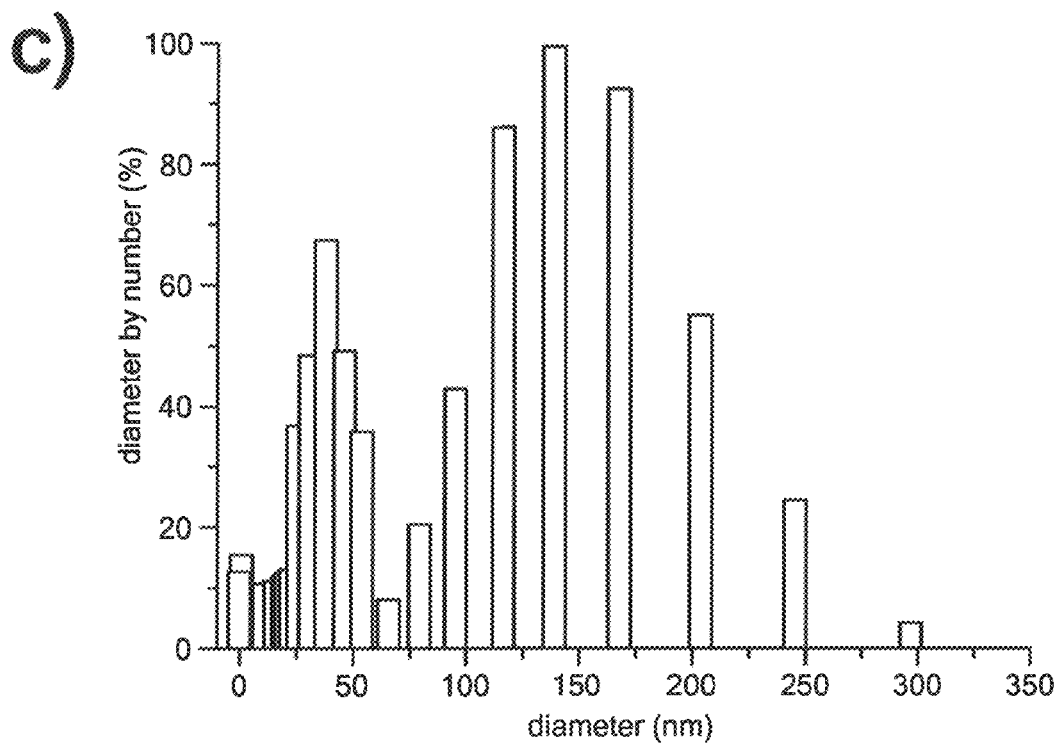
Figure 1D:
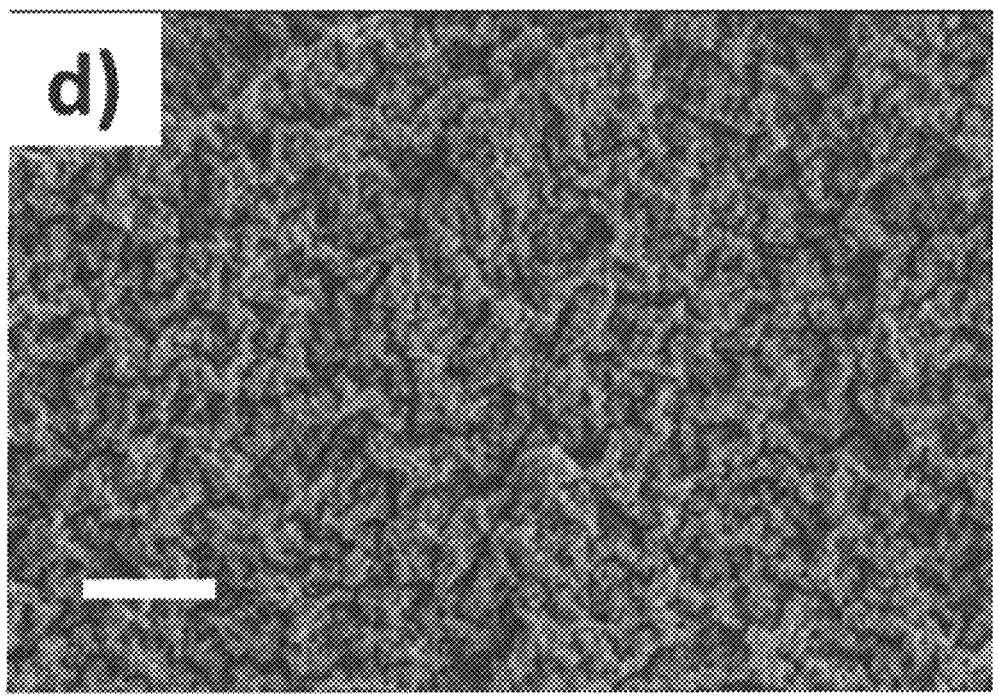

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, %, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Agent": As used herein, the term "agent" may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present disclosure include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

"Analog": As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance "Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Antibody": As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2. FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (and X) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is monoclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPsTM"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc]

"Associated" or "Associated with": As used herein, the term "associated" or "associated with" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example, streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Binding": It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

"Binding agent": In general, the term "binding agent" is used herein to refer to any entity that binds to a target of interest as described herein. In many embodiments, a binding agent of interest is one that binds specifically with its target in that it discriminates its target from other potential binding partners in a particular interaction contact. In general, a binding agent may be or comprise an entity of any chemical class (e.g., polymer, non-polymer, small molecule, polypeptide, carbohydrate, lipid, nucleic acid, etc). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptaviding and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding moiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise stapled peptides. In certain embodiments, binding agents are or comprise nucleic acids, such as DNA or RNA.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid) poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Biologically active": As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

"Characteristic portion": As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

"Comparable": The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer, those of ordinary skill in the art readily appreciate how to identify "corresponding" amino acids, including through use of one or more commercially-available algorithms specifically designed for polymer sequence comparisons.

"Detection entity": The term "detection entity" as used herein refers to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^{3}$H, $^{14}$C, $^{18}$F, $^{19}$F, $^{32}$, $^{35}$S, $^{135}$I, $^{125}$I, $^{123}$I, $^{64}$Cu, $^{87}$Re, $^{111}$In, $^{90}$Y, $^{99m}$Tc, $^{177}$Lu, $^{89}$Zr etc.), fluorescent dyes (for specific exemplary fluorescent dyes, see below), chemiluminescent agents (such as, for example, acridinium esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

"Determine": Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

"Dosage form": As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

"Encapsulated": The term "encapsulated" is used herein to refer to substances that are completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"Graft rejection": The term "graft rejection" as used herein, refers to rejection of tissue transplanted from a donor individual to a recipient individual. In some embodiments, graft rejection refers to an allograft rejection, wherein the donor individual and recipient individual are of the same species. Typically, allograft rejection occurs when the donor tissue carries an alloantigen against which the recipient immune system mounts a rejection response.

"High Molecular Weight Polymer": As used herein, the term "high molecular weight polymer" refers to polymers and/or polymer solutions comprised of polymers (e.g., protein polymers, such as silk) having molecular weights of at least about 200 kDa, and wherein no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Identity": As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

"Low Molecular Weight Polymer": As used herein, the term "low molecular weight polymer" refers to polymers and/or polymer solutions, such as silk, comprised of polymers (e.g., protein polymers) having molecular weights within the range of about 20 kDa-about 400 kDa. In some embodiments, low molecular weight polymers (e.g., protein polymers) have molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of, polymers having a molecular weight above about 400 kD. In some embodiments, the highest molecular weight polymers in provided hydrogels are less than about 300-about 400 kD (e.g., less than about 400 kD, less than about 375 kD, less than about 350 kD, less than about 325 kD, less than about 300 kD, etc). In some embodiments, a low molecular weight polymer and/or polymer solution can comprise a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, wherein the specified range is between about 3.5 kDa and about 120 kDa or between about 5 kDa and about 125 kDa.

"Marker": A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present disclosure a useful marker need not distinguish tumors of a particular subclass with 100% accuracy.

"Modulator": The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

"Nanoparticle": As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer.

"Nanoparticle composition": As used herein, the term "nanoparticle composition" refers to a composition that contains at least one nanoparticle and at least one additional agent or ingredient. In some embodiments, a nanoparticle composition contains a substantially uniform collection of nanoparticles as described herein.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refer to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present disclosure. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present disclosure is specifically directed to "unmodified nucleic acids," meaning nucleic acids (e.g., polynucleotides and residues, including nucleotides and/or nucleosides) that have not been chemically modified in order to facilitate or achieve delivery.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Polypeptide": The term "polypeptide", as used herein, generally has its art-recognized meaning of a polymer of at least three amino acids, linked to one another by peptide bonds. In some embodiments, the term is used to refer to specific functional classes of polypeptides. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. Alternatively or additionally, in many embodiments, such member also shares a particular characteristic sequence element with the reference polypeptide (and/or with other polypeptides within the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. In some embodiments, a polypeptide may comprise natural amino acids, non-natural amino acids, or both. In some embodiments, a polypeptide may comprise only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups, e.g., modifying or attached to one or more amino acid side chains, and/or at the polypeptide's N-terminus, the polypeptide's C-terminus, or both. In some embodiments, a polypeptide may be cyclic. In some embodiments, a polypeptide is not cyclic. In some embodiments, a polypeptide is linear.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of a porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Reference": The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a preferred small molecule is a therapeutic. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, the period of time is at least about one hour: in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

"Therapeutic agent": As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

"Therapeutically effective amount": As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

"Variant": As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

Among other things, the present disclosure provides silk fibroin-based hydrogels and methods of preparing and using such silk fibroin-based hydrogels. Various embodiments according to the present disclosure are described in detail herein. In particular, the present disclosure describes silk fibroin-based hydrogels and their use in various application, including, for example: biomaterials, biomedical, biosensing, drug delivery, electronics, optics, optogenetics, photonics, regenerative medicine, tissue engineering applications, tissue regeneration, utility for transparent tissues, and/or tunable degradation and/or controlled release applications.

Provided silk fibroin-based hydrogels are characterized by unique features that provide advantages over existing hydrogels. Silk fibroin-based hydrogels of the present disclosure exhibit optical clarity and/or optically transparent in the visible spectrum. Provided silk fibroin-based hydrogels have widely tunable mechanical properties. Provided silk fibroin-based hydrogels are characterized by tuning their mechanical properties so that they are capable of seeding and/or functionalization (e.g. with cells and/or other functional moieties). Provided silk fibroin-based hydrogels are non-toxic and biodegradable. Provided silk fibroin-based hydrogels are capable of being formed, molded, shaped, and/or machined into desired structures.

The reinvention of silk fibroin as a sustainable material for biomedical, optics, photonics and electronics applications has been predicated on the numerous material formats, for example, fibers, foams, particles, films, hydrogels, in which silk fibroin can be processed after regeneration in aqueous solution. (See H. Tao, 24 Adv. Mater., 2824-37 (2012) herein incorporated by reference in its entirety). Additionally, silk fibroin materials can be engineered with tunable morphological, physical, mechanical and biological properties by fine regulation of molecular weight at the point of protein extraction from silk fibers during the removal of sericin and by controlling the degree of crystallinity through exposure to heat, water vapor or polar solvents. (See H. Tao, 24 Adv. Mater., 2824-37 (2012) and F. G. Omenetto, 329 Science, 528-531 (2010) herein incorporated by reference in their entirety).

For optics and photonics applications, the film format for silk has generated interest due to transparency, robust mechanical properties and preservation of heat-labile sensing molecules encapsulated within the protein, allowing for the fabrication of optic and photonic devices with unprecedented features that can be interfaced with biology. (See F. G. Omenetto, 2 Nat. Photonics, 641-643 (2008) herein incorporated by referenced in its entirety. Conversely, other commonly used material formats of silk fibroin, such as foams and hydrogels are characterized by high optical loss due to internal light scattering. (See U. J. Kim, 5 Biomacromolecules, 786-92 (2004), S. Nagarkar, 12 Phys. Chem. Chem. Phys., 3834-44 (2010), and D. N. Rockwood, 6 Nat. Protoc., 1612-31 (2011) herein incorporated by reference in their entirety).

Silk hydrogels have been proposed as substrates for the engineering, modeling and regeneration of soft tissues, ranging from nerves to cartilage. (See P. H. G. Chao, 95 J. Biomed. Mater., Res. B. Appl. Biomater., 84-90 (2010) and A. M. Hopkins, 23 Adv. Funct. Mater., 5140-5149 (2013) hereby incorporated by reference in their entirety). There is in fact a need for soft biomaterials that match the physical and mechanical properties of human tissues by mimicking the hydrated nature of the extracellular space. (See J. L. Drury, 24 Biomaterials, 4337-4351 (2003), N. A. Peppas, 18 Adv. Mater., 1345-1360 (2006), and J. Zhu, 8 Expert Rev. Med. Devices, 607-26 (2011) herein incorporated by reference in their entirety). In addition, silk hydrogels can be easily modified to provide appropriate morphological, biochemical and mechanical cues and can be functionalized with stabilized heat-labile compounds. (See N. Guziewicz, 32 Biomaterials, 2642-50 (2011).

Hydrogels

In some embodiments, silk fibroin-based hydrogels are or comprise silk fibroin and/or silk fibroin fragments.

Silks

In some embodiments, a polymer is silk. Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, New Jersey (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta; Antheraea pernyi: Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata;* and *Nephila madagascariensis.*

In general, silk for use in accordance with the present disclosure may be produced by any such organism, or may be prepared through an artificial process, for example, involving genetic engineering of cells or organisms to produce a silk protein and/or chemical synthesis. In some embodiments of the present disclosure, silk is produced by the silkworm, *Bombyx mori.*

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | Antheraea mylitta | Salivary | Fibroin |
| AAC32606 | Antheraea pernyi | Salivary | Fibroin |
| AAK83145 | Antheraea yamamai | Salivary | Fibroin |
| AAG10393 | Galleria mellonella | Salivary | Heavy-chain fibroin (N-terminal) |
| AAG10394 | Galleria mellonella | Salivary | Heavy-chain fibroin (C-terminal) |
| P05790 | Bombyx mori | Salivary | Fibroin heavy chain precursor, Fib-H, H-fibroin |
| CAA27612 | Bombyx mandarina | Salivary | Fibroin |
| Q26427 | Galleria mellonella | Salivary | Fibroin light chain precursor, Fib-L, L-fibroin, PG-1 |
| P21828 | Bombyx mori | Salivary | Fibroin light chain precursor, Fib-L, L-fibroin |
| B. Spiders | | | |
| P19837 | Nephila clavipes | Major ampullate | Spidroin 1, dragline silk fibroin 1 |

TABLE 1-continued

An exemplary list of silk-producing species and silk proteins
(adopted from Bini et al. (2003), J. Mol. Biol. 335(1): 27-40).

| Accession | Species | Producing gland | Protein |
|---|---|---|---|
| P46804 | Nephila clavipes | Major ampullate | Spidroin 2, dragline silk fibroin 2 |
| AAK30609 | Nephila senegalensis | Major ampullate | Spidroin 2 |
| AAK30601 | Gasteracantha mammosa | Major ampullate | Spidroin 2 |
| AAK30592 | Argiope aurantia | Major ampullate | Spidroin 2 |
| AAC47011 | Araneus diadematus | Major ampullate | Fibroin-4, ADF-4 |
| AAK30604 | Latrodectus geometricus | Major ampullate | Spidroin 2 |
| AAC04503 | Araneus bicentenarius | Major ampullate | Spidroin 2 |
| AAK30615 | Tetragnatha versicolor | Major ampullate | Spidroin 1 |
| AAN85280 | Araneus ventricosus | Major ampullate | Dragline silk protein-1 |
| AAN85281 | Araneus ventricosus | Major ampullate | Dragline silk protein-2 |
| AAC14589 | Nephila clavipes | Minor ampullate | MiSp1 silk protein |
| AAK30598 | Dolomedes tenebrosus | Ampullate | Fibroin 1 |
| AAK30599 | Dolomedes tenebrosus | Ampullate | Fibroin 2 |
| AAK30600 | Euagrus chisoseus | Combined | Fibroin 1 |
| AAK30610 | Plectreurys tristis | Larger ampule-shaped | Fibroin 1 |
| AAK30611 | Plectreurys tristis | Larger ampule-shaped | Fibroin 2 |
| AAK30612 | Plectreurys tristis | Larger ampule-shaped | Fibroin 3 |
| AAK30613 | Plectreurys tristis | Larger ampule-shaped | Fibroin 4 |
| AAK30593 | Argiope trifasciata | Flagelliform | Silk protein |
| AAF36091 | Nephila madagascariensis | Flagelliform | Fibroin, silk protein (N-terminal) |
| AAF36092 | Nephila madagascariensis | Flagelliform | Silk protein (C-terminal) |
| AAC38846 | Nephila clavipes | Flagelliform | Fibroin, silk protein (N-terminal) |
| AAC38847 | Nephila clavipes | Flagelliform | Silk protein (C-terminal) |

Silk Fibroin

Fibroin is a type of structural protein produced by certain spider and insect species that produce silk. Cocoon silk produced by the silkworm, Bombyx mori, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of non-structural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the Bombyx mori fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained, from the cocoon of Bombyx mori. In some embodiments, spider silk fibroins are obtained, for example, from Nephila clavipes. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present disclosure contain fibroin proteins, essentially free of sericins. In some embodiments, silk solutions used to fabricate various compositions of the present disclosure contain the heavy chain of fibroin, but are essentially free of other proteins. In other embodiments, silk solutions used to fabricate various compositions of the present disclosure contain both the heavy and light chains of fibroin, but are essentially free of other proteins. In certain embodiments, silk solutions used to fabricate various compositions of the present disclosure comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk materials explicitly exemplified herein were typically prepared from material spun by silkworm, Bombyx mori. Typically, cocoons are boiled in an aqueous solution of 0.02 M $Na_2CO_3$, then rinsed thoroughly with water to extract the glue-like sericin proteins. Extracted silk is then dissolved in a solvent, for example, LiBr (such as 9.3 M) solution at room temperature. A resulting silk fibroin solution can then be further processed for a variety of applications as described elsewhere herein.

In some embodiments, polymers refers to peptide chains or polypeptides having an amino acid sequence corresponding to fragments derived from silk fibroin protein or variants thereof. In the context of hydrogels of the present disclosure, silk fibroin fragments generally refer to silk fibroin peptide chains or polypeptides that are smaller than naturally occurring full length silk fibroin counterpart, such that one or more of the silk fibroin fragments within a population or composition. In some embodiments, for example, silk fibroin-based hydrogels comprise silk fibroin polypeptides having an average molecular weight of between about 3.5 kDa and about 350 kDa. In some embodiments, suitable ranges of silk fibroin fragments include, but are not limited to: silk fibroin polypeptides having an average molecular weight of between about 3.5 kDa and about 200 kDa; silk fibroin polypeptides having an average molecular weight of between about 3.5 kDa and about 150 kDa; silk fibroin polypeptides having an average molecular weight of between about 3.5 kDa and about 120 kDa. In some embodiments, silk fibroin polypeptides have an average molecular weight of: about 3.5 kDa, about 4 kDa, about 4.5 kDa, about 5 kDa, about 6 kDa, about 7 kDa, about 8 kDa, about 9 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 105 kDa, about 110 kDa, about 115 kDa, about 120 kDa, about 125 kDa, about 150 kDa, about 200 kDa, about 250 kDa, about 300 kDa, or about 350 kDa. In some preferred embodiments, silk fibroin polypeptides have an average molecular weight of about 100 kDa.

In some embodiments, silk fibroin-based hydrogels are or comprise silk fibroin and/or silk fibroin fragments. In some embodiments, silk fibroin and/or silk fibroin fragments of various molecular weights may be used. In some embodiments, silk fibroin and/or silk fibroin fragments of various molecular weights are silk fibroin polypeptides. In some embodiments, silk fibroin polypeptides are "reduced" in size, for instance, smaller than the original or wild type counterpart, may be referred to as "low molecular weight silk fibroin." For more details related to low molecular weight silk fibroins, see: U.S. provisional application concurrently filed herewith, entitled "LOW MOLECULAR WEIGHT SILK FIBROIN AND USES THEREOF," the entire contents of which are incorporated herein by reference. In some embodiments, silk fibroin polypeptides have an average molecular weight of: less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, hydrogels of the present disclosure produced from silk fibroin fragments can be formed by degumming silk cocoons in an aqueous solution at temperatures of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, silk fibroin fragments solubilized prior to gelation. In some embodiments, a carrier can be a solvent or dispersing medium. In some embodiments, a solvent and/or dispersing medium, for example, is water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, fetal bovine serum, or suitable combinations and/or mixtures thereof.

In some embodiments, provided silk fibroin-based hydrogels are modulated by controlling a silk concentration. In some embodiments, a weight percentage of silk fibroin can be present in the solution at any concentration suited to the need. In some embodiments, an aqueous silk fibroin solution can have silk fibroin at a concentration of about 0.1 mg/mL to about 20 mg/mL. In some embodiments, an aqueous silk fibroin solution can comprise silk fibroin at a concentration of about less than 1 mg/mL, about less than 1.5 mg/mL, about less than 2 mg/mL, about less than 2.5 mg/mL, about less than 3 mg/mL, about less than 3.5 mg/mL, about less than 4 mg/mL, about less than 4.5 mg/mL, about less than 5 mg/mL, about less than 5.5 mg/mL, about less than 6 mg/mL, about less than 6.5 mg/mL, about less than 7 mg/mL, about less than 7.5 mg/mL, about less than 8 mg/mL, about less than 8.5 mg/mL, about less than 9 mg/mL, about less than 9.5 mg/mL, about less than 10 mg/mL, about less than 11 mg/mL, about less than 12 mg/mL, about less than 13 mg/mL, about less than 14 mg/mL, about less than 15 mg/mL, about less than 16 mg/mL, about less than 17 mg/mL, about less than 18 mg/mL, about less than 19 mg/mL, or about less than 20 mg/mL.

In some embodiments, a hydrogel is configured to be injectable. In some embodiments, a viscosity of an injectable composition is modified by using a pharmaceutically acceptable thickening agent. In some embodiments, a thickening agent, for example, is methylcellulose, xanthan gum, carboxymethyl cellulose, hydroxypropyl cellulose, carbomer, or combination thereof. A preferred concentration of the thickener depends upon a selected agent and viscosity for injection.

In some embodiments, hydrogel form a porous matrix or scaffold. For example, the porous scaffold can have a porosity of at least about 10%, at least about 20%, at least about 30%, at least about 40%, at least about 50%, at least about 60%, at least about 70%, at least about 80%, at least about 90%, or higher.

Degradation Properties of Silk-Based Materials

Additionally, as will be appreciated by those of skill in the art, much work has established that researchers have the ability to control the degradation process of silk. According to the present disclosure, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present disclosure encompasses the recognition that such degradability is also relevant to and useful in the fabrication of silk electronic components.

According to the present disclosure, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published (see, for example, WO 2004/080346, WO 2005/012606, WO 2005/123114, WO 2007/016524, WO 2008/150861, WO 2008118133, each of which is incorporated by reference herein).

Control of silk material production methods as well as various forms of silk-based materials can generate silk compositions with known degradation properties. For example, using various silk fibroin materials (e.g., microspheres of approximately 2 μm in diameter, silk film, silk hydrogels) entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

Crystalline Silk Materials

As known in the art and as described herein, silk proteins can stack with one another in crystalline arrays. Various properties of such arrays are determined, for example, by the degree of beta-sheet structure in the material, the degree of cross-linking between such beta sheets, the presence (or absence) of certain dopants or other materials. In some embodiments, one or more of these features is intentionally controlled or engineered to achieve particular characteristics of a silk matrix. In some embodiments, silk fibroin-based hydrogels are characterized by crystalline structure, for example, comprising beta sheet structure and/or hydrogen bonding. In some embodiments, provided silk fibroin-based hydrogels are characterized by a percent beta sheet structure within the range of about 0% to about 45%. In some embodiments, silk fibroin-based hydrogels are characterized by crystalline structure, for example, comprising beta sheet structure of about 1%, about 2%, about 3%, about 4%, about 5%, about 6%, about 7%, about 8%, about 9%, about 10%, about 11%, about 12%, about 13%, about 1%, about 1%, about 1%, about 1%, about 1%, about 1%, about 1%, about 1%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, or about 45%.

Nanosized Crystalline Particles

In some embodiments, silk fibroin-based hydrogels are characterized in that they comprise submicron size or nanosized crystallized spheres and/or particles. In some embodiments, such submicron size or nanosized crystallized spheres and/or particles have average diameters ranging between about 5 nm and 200 nm. In some embodiments, submicron size or nanosized crystallized spheres and/or particles have less than 150 nm average diameter, e.g., less than 145 nm, less than 140 nm, less than 135 nm, less than 130 nm, less than 125 nm, less than 120 nm, less than 115 nm, less than 110 nm, less than 100 nm, less than 90 nm, less than 80 nm, less than 70 nm, less than 60 nm, less than 50 nm, less than 40 nm, less than 30 nm, less than 20 nm, less than 15 nm, less than 10 nm, less than 5 nm, or smaller. In some preferred embodiments, submicron size or nanosized crystallized spheres and/or particles have average diameters of less than 100 nm.

Optical Transparency

In some embodiments, silk fibroin-based hydrogels exhibit optical clarity in visual spectrum. In some embodiments, silk fibroin-based hydrogels transmit light in a wavelength range between about 400 nm to about 800 nm. In some embodiments, provided silk fibroin-based hydrogels are between about 50% and 100% transparent in the visible spectrum. In some embodiments, silk fibroin-based hydrogels are characterized by having a high degree of transparency, e.g., about 20% to 99% transmittance in the visible spectrum (wavelengths ranging between about 400-700 nm). In some embodiments, silk fibroin-based hydrogels are at least 35% transparent in the visible spectrum, at least 40% transparent in the visible spectrum, at least 45% transparent in the visible spectrum, at least 50% transparent in the visible spectrum, at least 55% transparent in the visible spectrum, at least 60% transparent in the visible spectrum, at least 65% transparent in the visible spectrum, at least 70% transparent in the visible spectrum, at least 75% transparent in the visible spectrum, at least 80% transparent in the visible spectrum, at least 85% transparent in the visible spectrum, at least 90% transparent in the visible spectrum, at least 91% transparent in the visible spectrum, at least 92% transparent in the visible spectrum, at least 93% transparent in the visible spectrum, at least 94% transparent in the visible spectrum, at least 95% transparent in the visible spectrum at least 96% transparent in the visible spectrum, at least 97% transparent in the visible spectrum, at least 98% transparent in the visible spectrum, at least 99% transparent in the visible spectrum, or greater transparency in the visible spectrum as determined by methods described herein. In some embodiments, silk fibroin-based hydrogels of the present disclosure are characterized by optical transmittance greater that 93% in the visible spectrum.

In some embodiments, silk fibroin-based hydrogels are characterized as exhibiting crystallinity, nanosized crystalline particles, and optical transparency as described hereinabove at least part of which is facilitated by a sol-gel transition of a silk fibroin solution to a silk fibroin-based hydrogel via a nanogelation as provided herein.

In some embodiments, nanogelation of a silk fibroin solution to form silk fibroin-based hydrogels as provided herein occurs that mixing a silk fibroin solution with a polar organic solvent. In some embodiments, a polar organic solvent is or comprises acetone, ethanol, methanol, isopropanol, or combinations thereof. In some preferred embodiments, a polar organic solvent is acetone. In some embodiments, a silk fibroin solution has a concentration of about 0.1 mg/mL to about 20 mg/mL. In some preferred embodiments, a silk fibroin solution has a concentration of less than about 15 mg/mL. In some preferred embodiments, a silk fibroin solution has a concentration of less than about 10 mg/mL. In some embodiments, polar organic solvents drives the assembly of silk micelles into submicron-sized particles (<100 nm) to form silk fibroin-based hydrogels characterized as having optical transparency.

In some embodiments, silk fibroin-based hydrogels exhibit increase optical clarity when compared with traditional hydrogels, such as collagen based hydrogels.

Tunable Mechanical Properties

In some embodiments, silk fibroin-based hydrogels of the present disclosure are characterized by highly tunable mechanical properties. In some embodiments, silk fibroin-based hydrogels of the present disclosure are characterized in that they possess mechanical properties that are tunable to a particular desired range and/or set. In some embodiments, mechanical properties, in particular compressive strength and compressive modulus are tunable.

In some embodiments, a compressive strength of silk fibroin-based hydrogels is tunable in a range of between about 0.5 kPa and about 12 kPa without showing an indication of a plastic deformation. In some embodiments, silk fibroin-based hydrogels show a compressive strength of about 0.5 kPa, about 1 kPa, about 1.5 kPa, about 2 kPa, about 2.5 kPa, about 3 kPa, about 3.5 kPa, about 4 kPa, about 4.5 kPa, about 5 kPa, about 5.5 kPa, about 6 kPa, about 7 kPa, about 8 kPa, about 9 kPa, about 10 kPa, about 11 kPa, or about 12 kPa without showing an indication of a plastic deformation.

In some embodiments, a compressive modulus of silk fibroin-based hydrogels is tunable in a range of between about 0.5 kPa and about 20 kPa without showing an indication of a plastic deformation when measure at crosshead rates of: 0.100 mm/min, 0.200 mm/min, and/or 2.00 mm/min. In some embodiments, silk fibroin-based hydrogels show a compressive modulus of about 0.5 kPa, about 1 kPa, about 2 kPa, about 3 kPa, about 4 kPa, about 5 kPa, about 6 kPa, about 7 kPa, about 8 kPa, about 9 kPa, about 10 kPa, about 11 kPa, about 12 kPa, about 13 kPa, about 14 kPa, about 15 kPa, about 16 kPa, about 17 kPa, about 18 kPa, about 19 kPa or about 20 kPa without showing an indication of a plastic deformation when measure at crosshead rates of: 0.100 mm/min, 0.200 mm/min, or 2.00 mm/min.

In some embodiments, at least part of such elasticity or compressive ability may be facilitated by crosslinking agent. In some embodiments, a crosslinking agent is or comprises EDTA, or agent having a similar activity. In some embodiments, between about 1 mM and 100 mM EDTA may be used to carry out a crosslinking step. In some embodiments, about 5 mM, about 10 mM, about 15 mM, about 20 mM, about 30 mM, about 40 mM, or about 50 mM EDTA may be used to carry out crosslinking. In some embodiments, such crosslinking step may be carried out for about a few seconds, minutes, to hours.

In some embodiments, such a crosslinking step may be carried out by exposing a silk fibroin-based hydrogel as provided herein with a crosslinking agent, such as EDTA for about 0.5 hour, about 1.0 hour, about 1.5 hours, about 2.0 hours, about 2.5 hours, about 3.0 hours, about 3.5 hours, about 4.0 hours, about 4.5 hours, about 5.0 hours, about 5.5 hours, about 6.0 hours, about 6.5 hours, about 7.0 hours, about 7.5 hours, about 8.0 hours, about 8.5 hours, about 9.0 hours, about 9.5 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer.

In some embodiments, silk fibroin-based hydrogels with tunable properties are characterized in that they exhibit improved structural stability corresponding to increased compressive strength and/or increased compressive modulus. In some embodiments, at least part of such elasticity or compressive ability may be facilitated by crosslinking agent. In some embodiments, for example, one or more crosslinking agents may be used to achieve crosslinking of silk fibroin polypeptides, intra-molecularly, inter-molecularly, or both. Any suitable crosslinking agents may be used, including but are not limited to: an amine-to-amine crosslinker, amine-to-sulfhydryl crosslinker, carboxyl-to-amine crosslinker, photoreactive crosslinker, sulfhydryl-to-carbohydrate crosslinker, sulfhydryl-to-hydroxyl crosslinker, sulfhydryl-to-sulfhydryl crosslinker, or any combination thereof.

Functionalized Silk Fibroin-Based Hydrogels

In some embodiments, provided silk fibroin-based hydrogels exhibit tunable mechanical properties, which provides flexibility in downstream applications. In some embodiments, silk fibroin-based hydrogels of the present disclosure are characterized by mechanical properties that are particularly suitable for use in supporting cell growth, function, viability, and/or differentiation.

In some embodiments, silk fibroin-based hydrogels are characterized in that when seeded cells would culture on a hydrogel surface. In some embodiments, cells would remain viable for a period up to 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, or 65 days.

In some embodiments, silk fibroin-based hydrogels as provided herein are characterized by morphological features less than 100 nm. Such features have been previously demonstrated for stem cell differentiation (see M. J. Dalby, 6 Nat. Mater., 997-1003 (2007) herein incorporated by reference in its entirety), cell adhesion (see T. J. Webster, 20 Biomaterials, 1221-7 (1999) herein incorporated by reference in its entirety), and metabolic activity (see T. J. Webster, 21 Biomaterials, 1803-10 (2000) herein incorporated by reference in its entirety) and the fabrication of nanostructured silk fibroin-based hydrogels through nanogelation may be useful to probe biological activity.

In some embodiments, silk fibroin-based hydrogels are characterized in that when cell-seeded with human fibroblasts, cells showed alignment and increased production of fibrillar nanostructures in the extracellular space.

In some embodiments, silk fibroin-based hydrogels as provided are are capable of seeding and/or functionalization (e.g. with cells and/or other functional moieties). Provided silk fibroin-based hydrogels are non-toxic and biodegradable. Provided silk fibroin-based hydrogels are capable of being formed, molded, shaped, and/or machined into desired structures.

In some embodiments, silk fibroin-based hydrogels of the present disclosure are characterized by particular degradation properties. In some embodiments, silk fibroin-based hydrogels are degradable.

In some embodiments, silk fibroin-based hydrogels degrade with a rate that is dependent on a degree of crystallinity within provided silk fibroin-based hydrogels. In some embodiments, a high degree of crystallinity corresponds with longer biodegradation of the silk fibroin-based hydrogels. In some embodiments, silk fibroin-based hydrogels are tunable so that biodegradation of the silk fibroin may be modulated in vivo and in vitro from a period of hours to months to years. While not wishing to be bound to a theory, it is believed that enhanced crystallinity corresponds to a more packed, hydrophobic, structure that decreases accessibility by metalloproteinases (e.g. MMP1, MMP3, MMP9, MMP 13) and other proteolytic enzymes (e.g. chymotrypsin, trypsin) to cleavage sites in the protein (unpublished data).

In some embodiments, silk fibroin-based hydrogels degrade to release an agent useful for treatment of a disease, disorder, or condition.

In some embodiments, provided silk fibroin-based hydrogel of the present invention may be a three-dimensional (3D) structure, wherein at least one dimension of the 3D structure is at least than 10 micrometer.

In some embodiments, provided silk fibroin-based hydrogel may be a 3D structure comprising a predetermined microstructure fabricated therein and/or thereon. In some embodiments, such predetermined microstructure is a void. In some embodiments, such void may be or comprise a hole, a channel, a cavity, or any combination thereof.

In some embodiments, silk fibroin-based hydrogels of the present invention may have pores therein, i.e., a measurable degree of porosity. For example, in some embodiments, provided silk fibroin-based hydrogels have a porosity of between about 0% and 50%, e.g., about 5%, about 10%, about 15%, about 20%, about 25%, about 30%, about 35%, about 40%, about 45%, about 50%, etc. Suitable porogens, for example, may be used to achieve desired porosity.

In some embodiments, silk fibroin-based hydrogels as described herein are useful in regenerative medicine for transparent tissue scaffolds. In some embodiments, silk fibroin-based hydrogels are characterized in that they are capable of being seeded and/or functionalized. In some embodiments, silk fibroin-based hydrogels are characterized in that they are capable of being seeded and/or functionalized with cells, for example human cornea epithelial cells (HCECs). In some embodiments, silk fibroin-based hydrogels are characterized in that when seeded with cells they are capable of maintaining cell viability and proliferation over a period with no appreciable difference when compared to other hydrogels, such a collagen hydrogels. In some embodiments, silk fibroin-based hydrogels are characterized in that when seeded with cells they are capable of maintaining cell viability and proliferation over a period of between 14 and 28 days.

Provided silk fibroin-based hydrogels offer new opportunities at the intersection of biology and technology. Provided silk fibroin-based hydrogels can be valuably employed providing a new format of silk fibroin with beneficial attributes, for example, optical, mechanical, and/or structural properties. Silk fibroin-based hydrogels as provided herein are therefore particularly suitable as soft biomaterials characterized by physical and mechanical properties that are tunable to match a broad range of human tissues, for example from nerves to cartilage, by mimicking the hydrated nature of the extracellular space.

Indeed, the ability to combine optical clarity in the visible spectrum with the well-established, tunable biophysical, biochemical and biological properties of silk fibroin-based hydrogels shines a new light on hydrogels, enabling the engineering of highly tunable tissue-equivalent constructs with enhanced optical and photonic functionalities.

Methods of Forming Hydrogels

Silk fibroin sol-gel transition occurs through inter-molecular and intra-molecular interactions (mainly formation of hydrogen bonds and hydrophobic interactions) among protein chains, which fold from amorphous to thermodynamically stable β-sheets, driven by exposure of silk solutions to shear forces, electric fields, pH near or below the isoelectric point (pI=3.8-3.9), polar solvents, heat and water removal. (See U. J. Kim, 5 Biomacromolecules, 786-92 (2004) and S. Nagarkar, 12 Phys. Chem. Chem. Phys., 3834-44 (2010) herein incorporated by reference in their entirety). The soft-micelle assembly process is also regulated by the strong amphiphilic (hydrophobic and hydrophilic domains) nature of the protein, where short hydrophilic (amorphous) spacers intervene between large hydrophobic (crystallizable) blocks and play a critical role in preventing premature 0-sheet formation and in modulating water solubility. (See H. J. Jn, 424 Nature, 1057-61 (2003) herein incorporated by reference in its entirety).

Figure 11A:
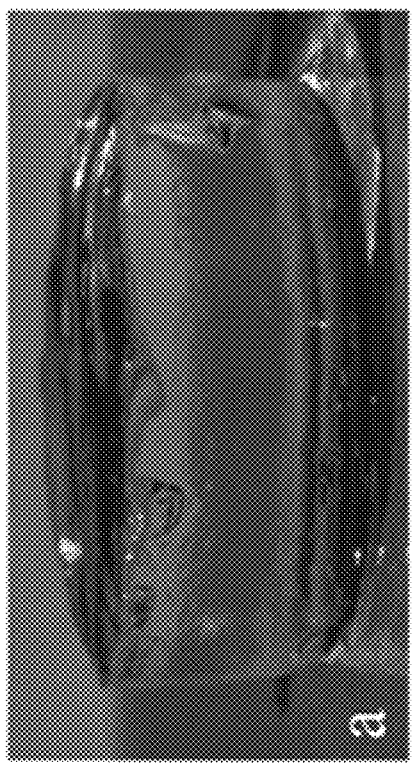
FIGS. 11A-11C show silk hydrogels.
Figure 11B:
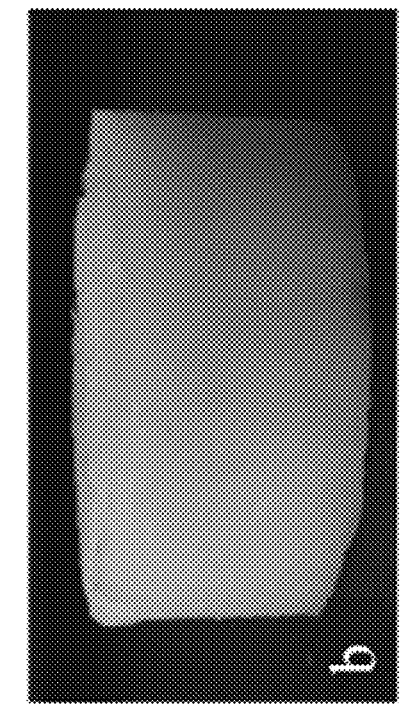
Figure 11C:
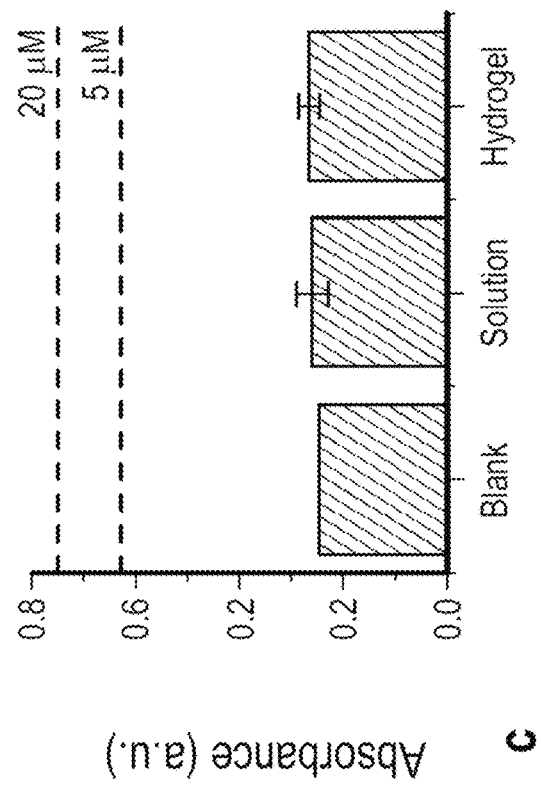

Development of inter-molecular bonds results in aggregation of silk fibroin micelles into interconnected micron-sized particles with progressive loss of transparency of the silk solution, ultimately becoming a white hydrogel due to light scattering (FIG. 11). Despite numerous applications of silk fibroin-based hydrogels in biomedical engineering, the lack of transparency has been of hindrance to fully capitalize on this material format. (See M. Choi, 7 Nat. Photonics, 987-994 (2013) herein incorporated by reference in its entirety). For example, biological entities (e.g. cells), light sensitive molecules (e.g. fluorescent, bioluminescent, photoactive macromolecules) and optogenetic tools can be incorporated into hydrogels for sensing and diagnostic applications, to generate biomimetic biological systems or to build optical interfaces with living tissues. Transparency is also the main characteristic of cornea tissue where silk fibroin has shown potential as scaffolding material for cornea replacements. (See T. Chirila, 561-565 Materials Science Forum, 1549-1552 (2007). T. V. Chirila, 14 Tissue Eng Part A, 1203-11 (2008), K. Higa, 27 Cornea, Suppl 1, S41-7 (2008), E. S. Gil, 10 Macromol. Biosci., 664-73 (2010), J. Wu, 35 Biomaterials, 3744-55 (2014). B. D. Lawrence, 8 Acta Biomater., 3732-3743 (2012), E. S. Gil, 31 Biomaterials, 8953-63 (2010), B. D. Lawrence, 30 Biomaterials, 1299-308 (2009) herein incorporated by reference in their entirety).

In some embodiments, fabrication of silk fibroin-based hydrogels as provided herein includes providing silk fibroin. In some embodiments, providing silk fibroin includes providing silk cocoons; boiling the silk cocoons in 0.02 M $Na_2CO_3$ to remove outer layers of sericin; cooling and unraveling cocoons into fibroin fibers; solubilizing fibers in a highly concentrated solution of chaotropic ions (LiBr); dialysizing the solution to remove the chaotropic salts from the solution, yielding a pure fibroin solution. Silk fibroin in solution possesses an amorphous structure (mostly random coils) and is arranged in micelles. In some embodiments, methods of forming silk fibroin-based hydrogels further includes mixing silk fibroin solution with acetone to form freestanding silk fibroin-based hydrogels. When the silk fibroin solution was exposed to polar solvents, a combination of amorphous-to-crystalline conformational changes together with aggregation results in the formation of silk particles, which arrange together in the presence of water forming a freestanding hydrogel structure.

Figures 2A, 2B:
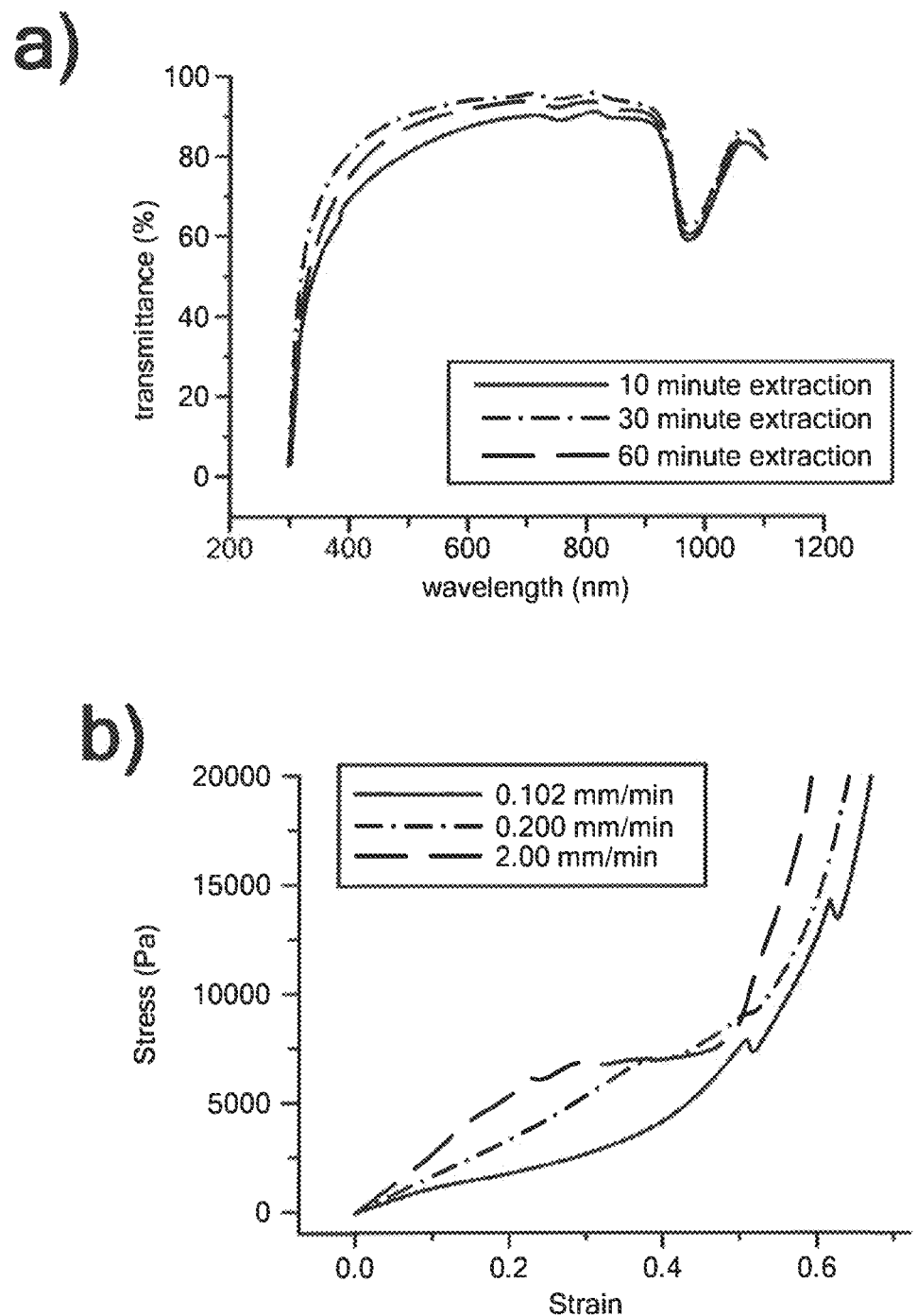
FIGS. 2A-2C show optical and mechanical properties of silk hydrogels.
Figures 7A, 7B, 7C:
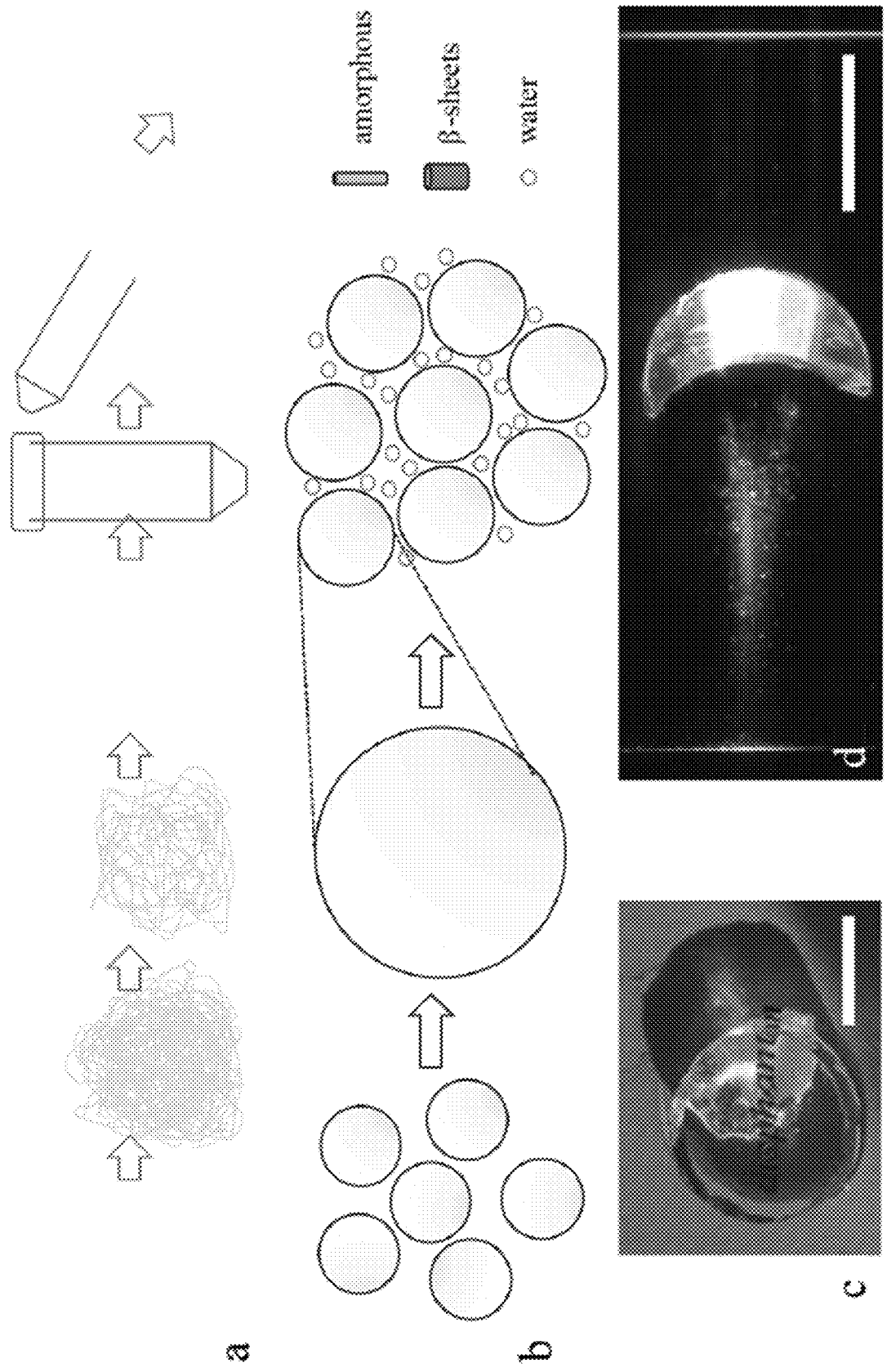

Nanogelation to induce the formation of a silk fibroin gel where the protein vesicles present in solution aggregate into nanosized particles during the sol-gel transition of the material, forming a transparent gel (FIG. 7(c), FIG. 2(a)) with defined shape and dimensions that are maintained upon removal from a mold. In addition, the method allows for the fabrication of hydrogels with convex or concave geometries that enable the formation of optical components such as a lens (FIG. 7(d)).

In some embodiments, the present disclosure also includes methods for making silk fibroin-based hydrogel described herein. Such a method may comprise steps of:

providing silk fibroin polypeptides; contacting the silk fibroin polypeptides with a polar organic solvent so as to induce beta-sheet formation in the silk fibroin polypeptides; boiling the polar organic solvent to cause formation of the silk fibroin-based hydrogel contemplated herein.

In some embodiments, suitable organic solvents include, but are not limited to: ketone-containing solvents, such as acetone.

In some embodiments, suitable organic solvents include, but are not limited to: ethanol, methanol, isopropanol, acetone, or combinations thereof.

In some embodiments, methods of forming silk fibroin-based hydrogels as provided herein, include steps of mixing two parts of silk fibroin solution (average molecular weight of 100 kDa, 10 mg/ml) with one part of acetone, where a relative concentration of silk fibroin to organic solvent is selected to maximize gel integrity and transparency. In some embodiments, acetone is successfully removed during processing and gelation in acetone provided enhanced transparency when compared to alcohols.

In some embodiments, methods for making silk fibroin-based hydrogel described herein may further include a step of crosslinking. In some embodiments, a step of crosslinking can be achieved by the use of one or more crosslinking agents. In some embodiments, any suitable crosslinking agents may be used. In some embodiments, crosslinking agents are or comprises EDTA, such as used at a concentration between about 5 mM and 100 mM, e.g., about 5 mM, about 10 mM, about 15 mM, about 20 mM, about 30 mM, about 40 mM, or about 50 mM EDTA.

In some embodiments, a crosslinking step may be carried out for a duration of time to induce sufficient level of crosslinking of silk fibroin polypeptides, e.g., for about 0.5 hour, about 1.0 hour, about 1.5 hours, about 2.0 hours, about 2.5 hours, about 3.0 hours, about 3.5 hours, about 4.0 hours, about 4.5 hours, about 5.0 hours, about 5.5 hours, about 6.0 hours, about 6.5 hours, about 7.0 hours, about 7.5 hours, about 8.0 hours, about 8.5 hours, about 9.0 hours, about 9.5 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer.

In some embodiments, matching, tuning, adjusting, and/or manipulating crystallinity, optical transparency, and/or mechanical properties of a silk fibroin-based hydrogels of the present disclosure is accomplished, at least in part, controlling, for example: by selecting a molecular weight of silk fibroin, by selecting a concentration of a silk fibroin solution, by selecting a solvent for a silk fibroin solution, by exposing silk fibroin-based hydrogels to polyamino carboxylic acids, such as (EDTA) at different concentrations and for different periods (e.g., durations), or by combinations thereof.

In some embodiments, a rate of degradation of a silk fibroin-based hydrogel may be controlled by selecting a molecular weight of a polymer, by selecting a polymer solution concentration, or combinations thereof.

In some embodiments, provided silk fibroin-based hydrogels are capable of being shaped into desirable forms, such as optical components. Additionally or alternatively, in some embodiments, provided silk fibroin-based hydrogels may be altered internally and/or on the surface by suitable techniques, such as direct laser writing.

Accordingly, the present invention encompasses methods for fabricating silk fibroin-based hydrogels for various applications. In some embodiments, such methods may include steps of: providing the silk fibroin-based hydrogel contemplated herein; machining a predetermined microstructure in and/or on the silk fibroin-based hydrogel. In some embodiments, the step of machining is performed with a laser.

In some embodiments, silk fibroin-based hydrogels and related methods provided herein may be useful for a wide range of products, processes, services and/or research tools. To name but a few, such embodiments can be used as drug release gels or bulk optical components (such as lenses, diffraction gratings, or microprism arrays). In some embodiments, silk fibroin-based hydrogels and related methods embraced herein may be useful for a variety of biomedical and/or clinical applications, including but are not limited to: scaffold fillers for tissue, scaffold research tools to visualize cell growth and interaction, even at depths over 1 mm for culture models.

Functional Moieties and/or Agents

In some embodiments, provided hydrogels can comprise one or more (e.g., one, two, three, four, five or more) agents and/or functional moieties (together, "additives"). Without wishing to be bound by a theory additive can provide or enhance one or more desirable properties, e.g., strength, flexibility, ease of processing and handling, biocompatibility, bioresorability, surface morphology, release rates and/or kinetics of one or more active agents present in the composition, and the like. In some embodiments, one or more such additives can be covalently or non-covalently linked with the hydrogel (e.g., with a polymer such as silk fibroin that makes up the hydrogel) and can be integrated homogenously or heterogeneously within the silk composition.

In some embodiments, an additive is or comprises a moiety covalently associated (e.g., via chemical modification or genetic engineering) with a polymer. In some embodiments, an addivity is non-covalently associated with a hydrogel or hydrogel component.

In some embodiments, provided hydrogels comprise additives at a total amount from about 0.01 wt % to about 99 wt %, from about 0.01 wt % to about 70 wt %, from about 5 wt % to about 60 wt %, from about 10 wt % to about 50 wt/o, from about 15 wt % to about 45, wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided hydrogels include one or more additives at a molar ratio relative to polymer (i.e., a polymer:additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety polymer:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety polymer:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, provided hydrogels comprise additives, for example, therapeutic, preventative, and/or diagnostic agents.

In some embodiments, an additive is or comprises one or more therapeutic agents. In general, a therapeutic agent is or comprises a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or comprises an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypetensive, sedative, birth control agent, progestational agent, anti-cholinergic, analgesic, anti-depressant, anti-psychotic, f-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, provided hydrogels comprise additives, for example, cells. Cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

In some embodiments, provided hydrogels comprise additives, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

In some embodiments, provided hydrogels comprise additives, for example, antibiotics. Antibiotics suitable for incorporation in hydrogels include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridinc, cephalothin, moxalactam, piperacillin, ticarcillin and combination thereof.

In some embodiments, provided hydrogels comprise additives, for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex) @); rofecoxib (VioxxW), etoricoxib (Arcoxia@t), meloxicam (Mobic)), valdecoxib, diclofenac (Voltaren@, Cataflam@), etodolac (Iodine@), sulindac (Clinori), aspirin, alclofenac, fenclofenac, diflunisal (Dolobid@), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbipofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldcne®), indomethacin (Indocin®), nabumetone (Relafen®), naproxen (Naprosynk), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, provided hydrogels comprise additives, for example, antibodies. Suitable antibodies for incorporation in hydrogels include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, provided hydrogels comprise additives, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided hydrogels comprise additives, for example, particularly useful for wound healing. In some embodiments, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided hydrogels comprise additives, for example, an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protothodopsin, and porphyrins; light capturing complexes such as phycobiliproteins; and related electronically active compounds; and combinations thereof.

Nucleic Acids

In some embodiments, provided hydrogels comprise additives, for example, nucleic acid agents. In some embodiments, a hydrogel may release nucleic acid agents. In some embodiments, a nucleic acid agent is or comprises a therapeutic agent. In some embodiments, a nucleic acid agent is or comprises a diagnostic agent. In some embodiments, a nucleic acid agent is or comprises a prophylactic agent.

It would be appreciate by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or comprise deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or comprises at least one protein-coding element. In some embodiments, a nucleic acid has a nucleotide sequence that is or comprises at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiment, a nucleic acid agent is or comprises an oligonucleotide. In some embodiments, a nucleic acid agent is or comprises an antisense oligonucleotide. Nucleic acid agents may include a chemical modification at the individual nucleotide level or at the oligonucleotide backbone level, or it may have no modifications.

In some embodiments of the present disclosure, a nucleic acid agent is an siRNA agent. Short interfering RNA (siRNA) comprises an RNA duplex that is approximately 19 basepairs long and optionally further comprises one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to comprise sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase lB (PTPIB).

Growth Factor

In some embodiments, provided hydrogels comprise additives, for example, growth factor. In some embodiments, a hydrogel may release growth factor. In some embodiments, a hydrogel may release multiple growth factors. In some embodiments growth factor known in the art include, for example, adrenomedullin, angiopoictin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided hydrogels comprise additives, for example, that are particularly useful for healing. Exemplary agents useful as growth factor for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), ApligrafW (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF;

IGF-1, proinflammatory cytokines, GM-CSF, and leptins and 6) IGF-1 and KGF cDNA, autologous platelet gel, hypochlorous acid (SteriloxV lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm$^T$M, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that agents useful for growth factor for healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, provided hydrogels comprise additives, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, provided hydrogels comprise additives, for example, radionuclides that are particularly useful as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming thermally-responsive conjugates in accordance with the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. In some embodiments, a diagnostic agent may be a fluorescent, luminescent, or magnetic moiety.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, rcef coral fluorescent protein, etc. Luminescent proteins include luciferase, acquorin and derivatives thereof. Numerous fluorescent and luminescent dyes and proteins are known in the art (see, e.g., U.S. Patent Application Publication No.: 2004/0067503; Valeur, B., "Molecular Fluorescence: Principles and Applications," John Wiley and Sons, 2002; *Handbook of Fluorescent Probes and Research Products, Molecular Probes*, 9$^{th}$ edition, 2002; and *The Handbook—A Guide to Fluorescent Probes and Labeling Technologies*, Invitrogen, 10$^{th}$ edition, available at the Invitrogen web site; both of which are incorporated herein by reference).

EXEMPLIFICATION

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

The present Example describes synthesis and characterization of an insoluble transparent silk fibroin-based hydrogels with tunable mechanical properties to be used for tissue engineering applications.

Materials and Methods

Silk fibroin solution preparation.

*B. mori* silkworm cocoons were boiled for 30 minutes in a solution of 0.02 M Na$_2$CO$_3$ to remove the sericin glycoprotein. The extracted fibroin was rinsed in deionized water and set to dry for 12 h. The dried fibroin was dissolved in 9.3 M LiBr solution at 60° C. for 3 h. The solution was dialyzed against deionized water using a dialysis cassette (Slide-a-Lyzer, Pierce, MWCO 3.5 KDa) at room temperature for 2 days until the solution reaches a concentration of ~60 mg/ml. The obtained solution is purified using centrifugation and filtered through a 5 μm syringe filter.

Silk Hydrogel Synthesis

Acetone Optima (Fisher Scientific) was used to synthesis the hydrogel. Acetone was set in a glass Petri dish and varying concentrations of silk solution (7.5 mg/ml, 10 mg/ml, 15 mg/ml 20 mg/ml, 30 mg/ml) were added to the acetone bath. The ratio of silk solution to acetone was in this experiment was not more than 2:1. The acetone was evaporated at room temperature (flashed off) for 12 h while adding deionized water to prevent the gel from collapsing. The hydrogel was soaked in a 20 mM solution of ethylenediaminetetraacetic acid (EDTA) (pH=8.5, Sigma Aldrich) for different time periods up to 24 h to increase the gel stiffness. The gels were rinsed in deionized water again to remove any access EDTA.

Results

Since previous literature shows that adding silk fibroin to organic solvents generates crystallized spheres, SEM and DLS measurements is used to characterize the structure and morphology of these gels. The optically transparent gels are composed of submicron spheres ranging in diameters from 10 nm to 135 nm depending on the molecular chain length (based on silk extraction time) and the concentration of silk solution.

In the visible spectrum (400-700 nm), 93% transmittance was attained through a 1 cm thick sample. FIG. 2(a) shows transmission of silk hydrogels with silk boil times of 10 minutes, 30 minutes, and 60 minutes. Silk concentrations of 2 wt % at different molecular weights provide greater than 80% transmittance while increasing silk concentration decreased the transmittance to below 40%.

FIG. 2(b) shows stress-strain curves of silk hydrogels at crosshead rates of 0.102 mm/min, 0.200 mm/min, and 2.000 mm/min for 30 minute boil silk. Each curve represents a hydrogel cross-linked in EDTA for 24 hrs. The unconfined compressive modulus of silk hydrogels was measured using an Instron 3366 testing frame (Instron, Norwood, MA) with crosshead speeds of 0.102 mm/min, 0.200 mm/min, and 2.000 mm/min using a 10 N capacity load cell conducted in air between force plates. The linear elastic modulus was calculated using a least-squared fitting in the linear region. The compressive modulus of the hydrogels correlates with the final silk concentration and with the addition of chemical crosslinking agents. Changing the amount of time spent in the crosslinking agent increases the compressive modulus of the hydrogels without affecting its optical transparency.

Figure 2C:
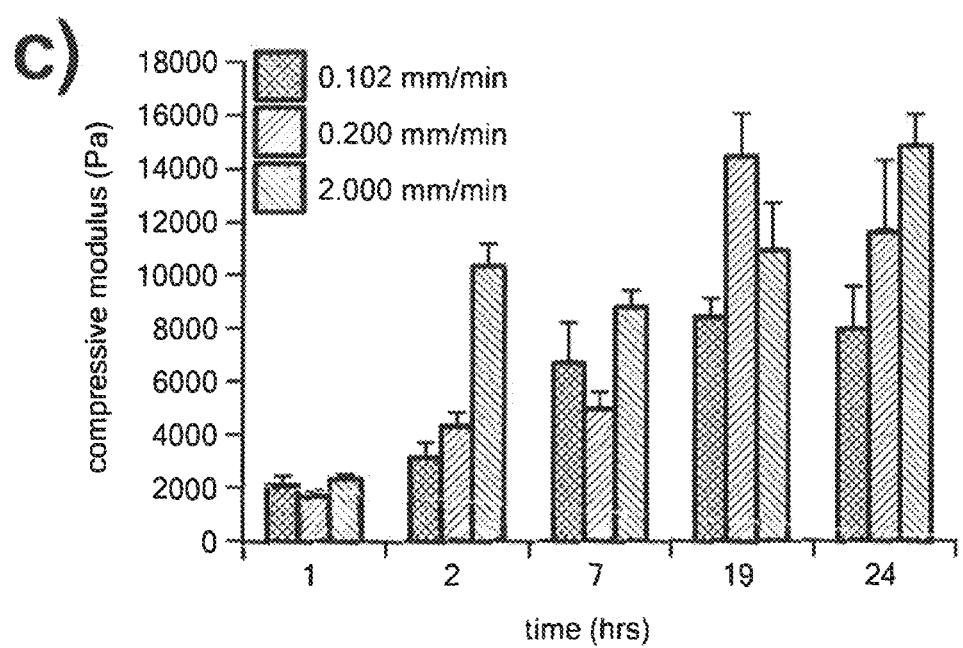

FIG. 2(c) shows analysis of the compressive modulus of silk hydrogels as a function of time spent in 20 mM EDTA solution for individual crosshead rate. Hydrogels cross-linked in EDTA for 1 hr, 2 hr, 7 hr, 19 hr, and 24 hrs, had unconfined compressive moduli of 2.3±0.1 kPa, 10.3±0.7 kPa, 8.8±0.4 kPa, 10.9±1.7 kPa, and 14.7±1.1 kPa respectively with a crosshead speed of 2.000 mm/hr.

Figure 3:
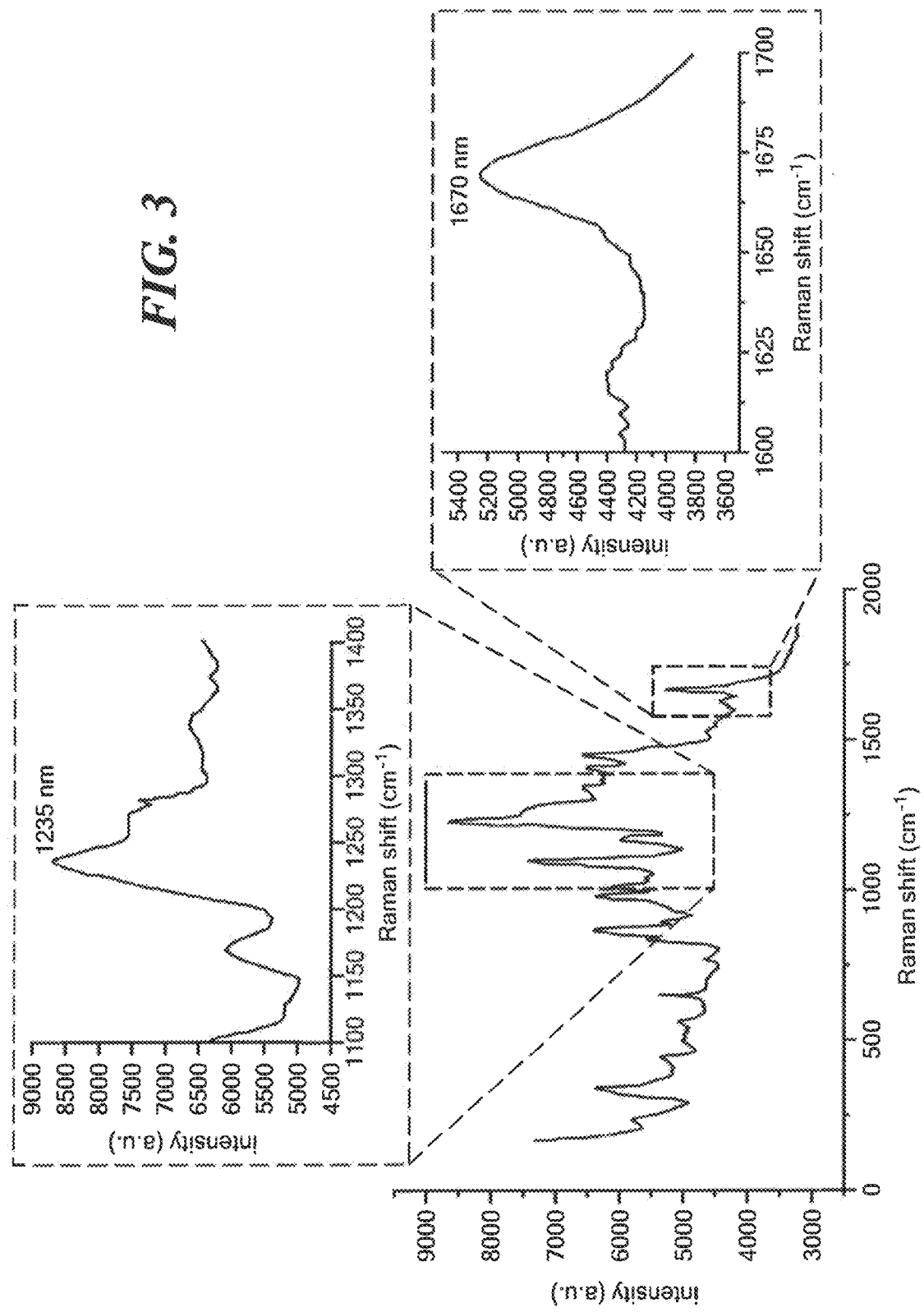
FIG. 3 shows the Raman spectrum of a silk hydrogel. To emphasize the β-sheet peaks, magnified spectra are shown for 1100-1400 cm$^{-1}$ and 1600-1700 cm$^{-1}$.

FIG. 3 shows the Raman spectrum of a silk hydrogel. Raman spectroscopy shows the amide I band at 1670 cmr and the narrow amide III band centered at 1230 $cm^{-1}$ which are characteristic of polypeptide chains in a β-sheet conformation.

Figure 4:
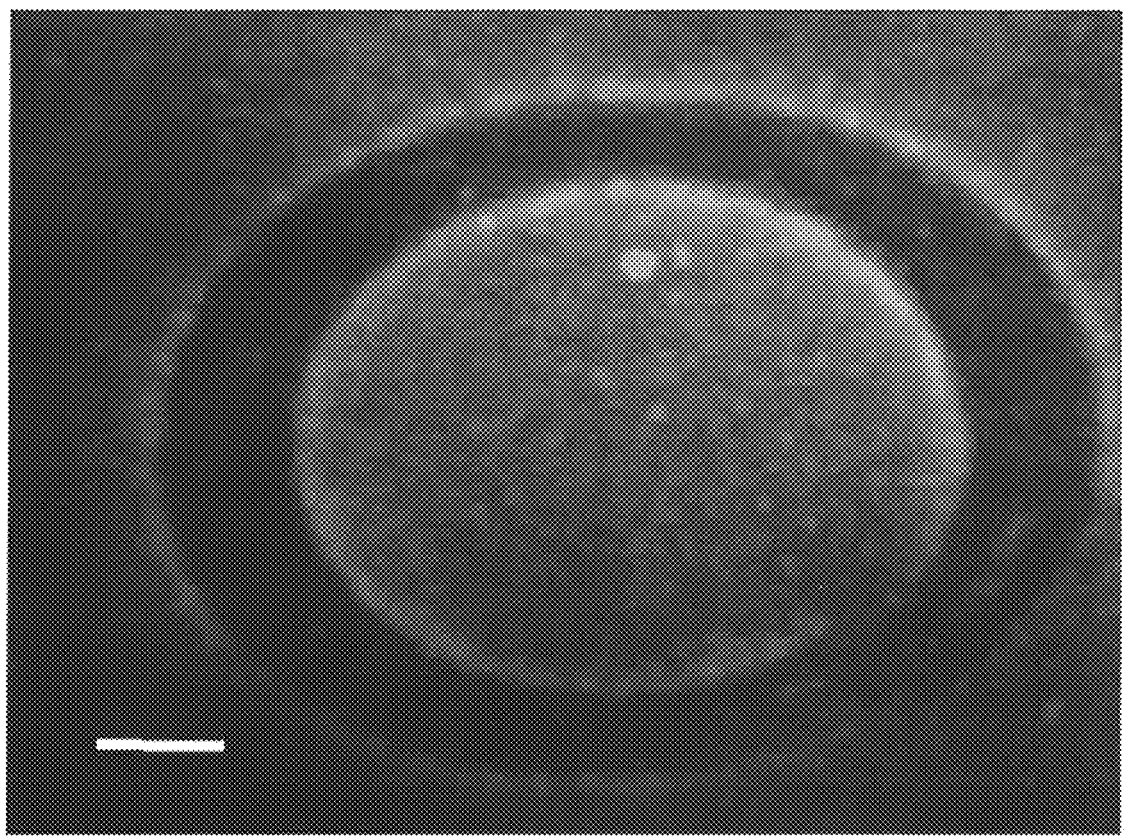
FIG. 4 shows a helix micro channel laser machined in a silk hydrogel. Scale bar is 40 μm.

Due to the transparency of the gels, they are easily machined by direct laser writing (DLW). DLW is a process by which highly focused laser beams alter a material at the micro scale. This method relies on multiphoton absorption to limit the influence of the beam only to the volume of material within the focal spot. By adjusting the power and beam shape, features can be created at resolutions higher than the diffraction limit. Utilizing this technique, predefined internal microstructures can be generated in bulk silk fibroin-based hydrogels. We present a method for the creation of microstructures, such as microtubules in a bulk 3D silk fibroin gel to depths of up to 1 mm. FIG. 4 shows a helix micro channel laser machined in a silk hydrogel. Scale bar is 40 μm.

Figures 5A, 5B:
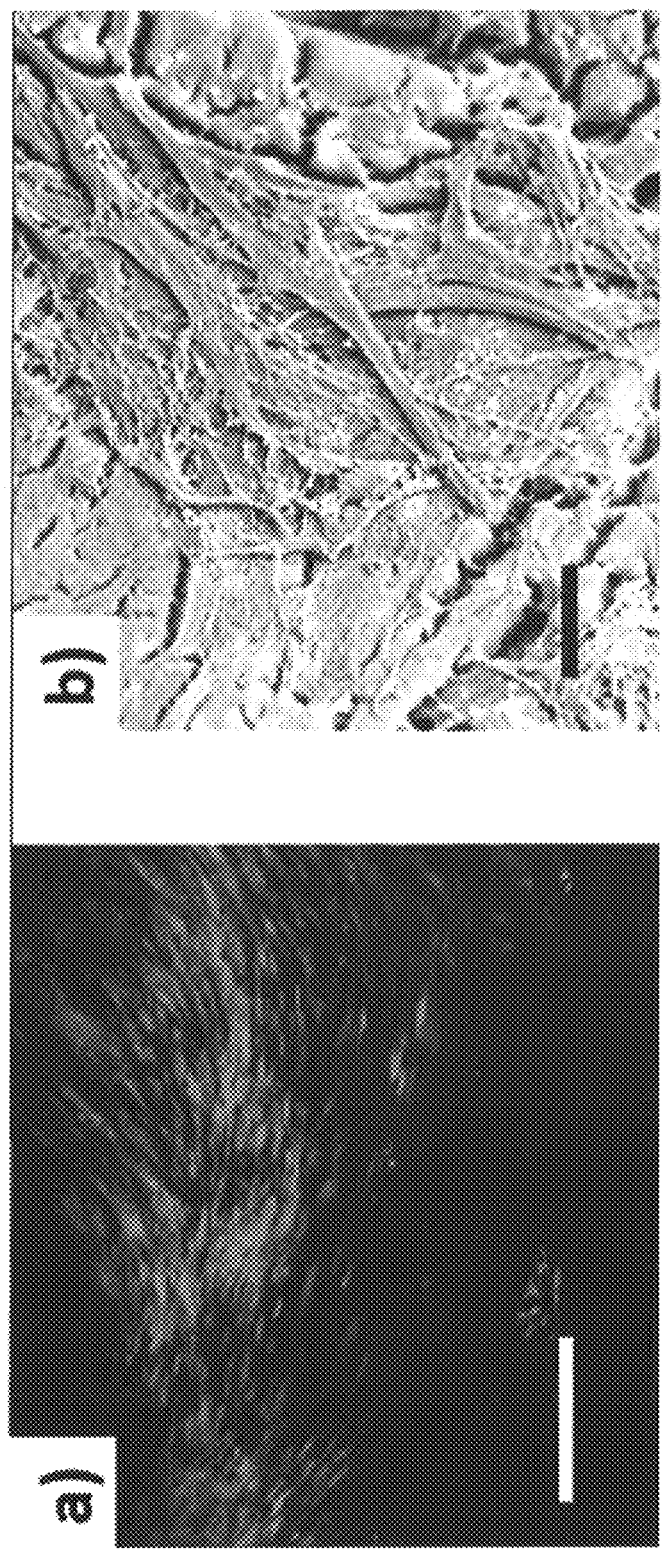
FIGS. 5A-5B show imaging of silk hydrogels.

Since the hydrogel is composed of a peptide sequence, unmodified hydrogels are capable of growing human fibroblasts up to 28 days in culture. Human fibroblasts attached to the surface of the hydrogels effectively in an attempt to remodel the matrix by aligning themselves against each other. FIG. 5(a) shows a confocal microscope image of live dermal fibroblasts on the hydrogel surface after 7 days. Scale bar is 375 μm. FIG. 5(b) shows an SEM image of fibroblasts attached on the hydrogel surface. Scale bar is 20 μm. Fibroblasts also penetrate several hundreds of microns within the hydrogels when a porogen was added forming spaces for fibroblasts to proliferate.

Figure 6A:
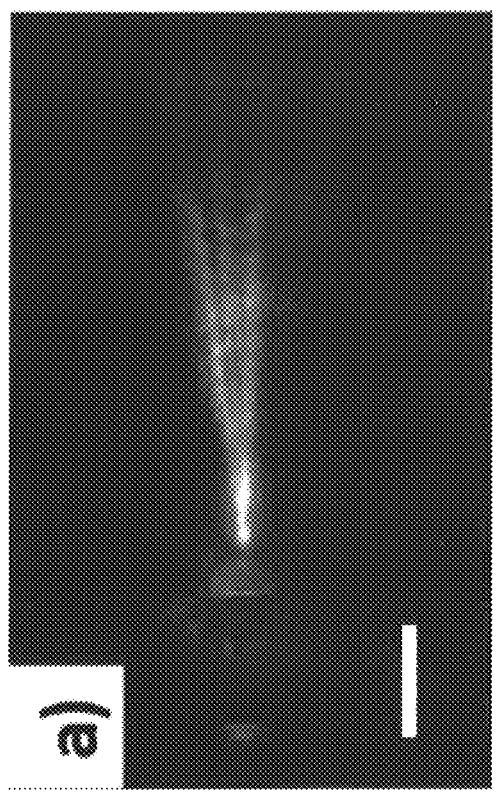
FIGS. 6A-6B show images of optical output through silk hydrogel optical components.
Figure 6B:

The optical clarity of the hydrogels allows this material to be fabricated into large optical components such as lenses with varying focal length and refractive index. The soft elastic modulus of the hydrogel allows the lenses to be molded into any shape with tunable focal lengths when the gels are under compression or tension, or when in the hydrogel absorbs fluids of different refractive indices. FIG. 6(a) shows a top view of a converging lens fabricated from a silk hydrogel without fibroblasts on the surface. The focal length of the lens is approximately 1.5 mm. Scale bar is 1 cm. FIG. 6(b) shows a top view of a diverging lens fabricated from a silk hydrogel without fibroblasts on the surface. The focal length of the lens is approximately 1.5 mm. Scale bar is 1 cm.

Example 2

The present Example describes induced nanogelation of a silk fibroin solution where protein vesicles present in solution were aggregated into nanosized particles during a sol-gel transition to form a transparent gel with defined shape and dimensions that are maintained upon removal from a mold.

Materials and Methods

Silk Fibroin Solution Preparation

Silk fibroin solution was prepared as previously described in FIG. 7(a). B. mori silkworm cocoons were boiled for 30 minutes in a solution of 0.02 M $Na_2CO_3$ to remove the sericin glycoprotein. The extracted fibroin was rinsed in deionized water and set to dry for 12 h. The dried fibroin was dissolved in 9.3 M LiBr solution at 60° C. for 3 h. The solution was dialyzed against deionized water using a dialysis cassette (Slide-a-Lyzer, Pierce. MWCO 3.5 kDa) at room temperature for 2 days until the solution reached a concentration of ~60 mg/ml. The obtained solution was purified to remove large aggregates using centrifugation and filtered through a 5 μm syringe filter.

Hydrogel Preparation

Acetone Optima (Fisher Scientific) was used to synthesize the hydrogels. Acetone was set in a glass Petri dish and silk solution with a concentration of 10 mg/ml was added to an acetone bath as previously described in FIG. 7(a). The ratio of silk solution to acetone was of 2:1. The acetone was evaporated at room temperature while adding deionized water to exchange with the gels and to prevent gel collapse. To improve the mechanical properties of the hydrogels, the hydrogels were soaked in a 20 mM solution of ethylenediaminetetraacetic acid (EDTA) (pH=8.5, Sigma Aldrich) for different time lengths from 1 h2 h, 7 h, 19 h, and 24 h. The hydrogels were rinsed in deionized water to remove any excess EDTA. Type I collagen hydrogels (FirstLink UK, 2.1 mg/ml) were prepared as previously described and were used as control for cell culture.

Morphological Characterization

SEM was used to evaluate scaffold morphology. All SEM micrographs were taken with a Supra55VP FESEM (Zeiss) using the in-lens SE detector. Morphological characterization of the hydrogels was obtained by drying the samples in hexamethyldisilazane (HMDS). Samples were first dehydrated in a series of ethanol rinses at concentrations of 50%, 70%, 80%, 90%, 95%, 100%, and 100% for 30 minutes and then exposed to a series of HMDS baths at 70%, 90%, 100%, and 100% for 30 minutes to ensure complete saturation in HMDS. Samples were then left to dry in a chemical hood for 12 hours to allow complete evaporation of HMDS and then immediately sputter coated and imaged at 3 kV.

Physical Characterization

For light transmission measurements, visible spectra were taken using a vis/near-infrared fiber-optic spectrometer (USB-2000, Ocean Optics). White light was propagated through the fiber to pass through the sample, and the transmitted light was coupled into a fiber tip guided to the spectrometer. The distance between the illumination source and the collection tip was fixed at 10 mm. All samples had a thickness of 4 mm.

Dynamic light scattering (DLS) experiments were conducted using a Brookhaven Instrument B1200-SM goniometer (Holtsville, NY, USA) equipped with a diode laser operated at a wavelength of 532 nm. DLS analysis of the silk nanoparticles were mixed in glass vials at concentrations of 10 mg/ml, 20 mg/ml, 40 mg/ml, and 60 mg/ml and analyzed before gelation. Quantitative analysis of the distribution of relaxation times and corresponding size distributions were obtained using the Non-Negative Least Squares: Multiple Pass (NNLS) method. (See X. Wang, et al., 31 Biomaterials, 1025-35 (2010) the entire contents of which are herein incorporated by reference). The size distribution extrapolated by the DLS was set to a weighted average to calculate the average diameter.

Raman Microscopy Measurements

μRaman spectra were collected using a JASCO NRS 3100 laser Raman spectrophotometer (JASCO. Tokyo, Japan). Hydrogels were mounted on a glass microscope slide and excited at 784 nm with a laser focused using a 100× objective. Spectra were obtained by measuring from 1800 $cm^{-1}$ to 200 $cm^{-1}$ using a resolution of 0.5 $cm^{-1}$, and 5 accumulations per sample with an exposure time of 20 s.

Mechanical Characterization

Compressive properties of silk fibroin-based hydrogel were measured using an Instron 3366 testing frame (Instron, Norwood, MA) with crosshead rates of 0.100 mm/min, 0.200 mm/min, and 2.000 mm/min with a 10 N capacity load cell. Samples were conducted in air between displacement plates until maximum compression was reached (load limit set at 7 N). Compressive modulus was calculated using a least-squared fitting in the linear region of initial compression in the 5%-20% strain range or before the yield strength was reached.

Cell Culture

Human dermal fibroblasts (HDFa, Invitrogen) were cultured on the silk hydrogels after treatment in ethanol for 24 h. Samples were rinsed in 3 subsequent PBS baths, pH=7.4 before cell seeding at a density of 20,000 cells/cm2. Cultures were grown to confluence in Dulbecco's Modified Eagle Medium (DMEM), high glucose, GlutaMAX™ Supplement (Invitrogen), 10% fetal bovine serum (FBS), and 1% penicillin/streptomycin antibiotic (Invitrogen) maintained at 37° C. in humidified atmosphere of 5% $CO_2$.

Human corneal epithelial cells (HCEC), isolated from the progenitor-rich limbal region of the eye, were purchased from Invitrogen. HCECs were cultured in Keratinocyte Serum Free Medium (Invitrogen) supplemented with 1% penicillin/streptomycin antibiotic at 37° C. in humidified atmosphere of 5% $CO_2$. HCECs at passage 3 were detached from tissue culture plastic using TrypLE™ Express (Invitrogen) and then reseeded on silk hydrogels and collagen hydrogels at a density of 25,000 cells/$cm^2$. Cultures were incubated at 37° C. for 3 h allowing the cells to attach to the hydrogel surface before the addition of media.

Metabolic Activity

AlamarBlue™ reagent was used to assess HCECs metabolic activity on silk fibroin-based hydrogel surfaces at days 1, 3, 7, and 10 in culture. Type I collagen hydrogels were used as control. For metabolic activity, samples were incubated in complete culture medium with 10% AlamarBlue™ reagent (Invitrogen, USA) at 37° C. for 4 h. Post incubation, 100 μl aliquots of media were collected in triplicate from quadruple samples and the fluorescence detection, indicative of cellular reduction of resazurin indicator, was measured at 590 nm using 530 excitation using a microplate reader (SpectrMax M2, Molecular Devices, Sunnyvale, CA, USA). Acellular scaffolds were used as the background reference.

Cell Imaging

Confocal images were taken with a Leica DMIRE2 confocal laser-scanning microscope (Wetzlar, Germany). Live/dead sample staining was conducted using a LIVE/DEADR Cell Viability/Cytotoxicity Kit (Life Technologies. Grand Island, NY, USA) by incubating a solution containing 2 μM calcein AM and 4 μM Ethidium homodimer-I ($EthD^{-3}$) for 60 minutes at 37° C. Samples were excited at 488 nm and emission at 510-530 nm for live cells (green) and excitation at 543 nm and emission for dead cells at 610-640 nm (red).

For SEM analysis, cellular hydrogels were removed from each culture well and fixed in 10% buffered formalin and let to sit for 12 h at 4° C. Samples were then removed and washed with 3 subsequent PBS (pH 7.4) rinses before dehydration in a series of ethanol solutions at 50%, 70%, 80%, 90%, 95%, 100%, and 100% for 30 minutes. Samples were then critically point dried using an Auto Samdri 815 Series A (Tousimis, Rockville, MD) operating above the critical point of liquid carbon dioxide. All samples were sputter coated using platinum/palladium and imaged at 3 kV.

Acetone Detection

Salicylaldehyde was used to measure trace amounts of acetone within the hydrogel samples. 0.4 ml of 10.6 M sodium hydroxide was added to the hydrogel samples before diluting the solution with 5 ml of water. The solution was mixed and 0.12 ml of salicylaldehyde was added to the solution of 4 ml of 10.6 M sodium hydroxide was added, and the solution was incubated at room temperature for 2 hours before the absorbance was measured at 474 nm. The amount of acetone in the samples was evaluated from a standard curve prepared as previously described. (See S. Berntsson, 28 Anal. Chem., 1337 (1956) the entire contents of which are herein incorporated by reference).

Fourier transform infrared spectroscopy FTIR analysis of hydrogel samples was performed in a JASCO FTIR 6200 spectrometer (JASCO, Tokyo, Japan) in attenuated total reflectance (ATR). Hydrogels were let to dry on a glass slide. For each sample, 64 scans were coded with a resolution of 1 $cm^{-1}$, with a wave number range from 4000-650 s $cm^{-1}$.

Statistical Analysis

All data were statistically compared with one way ANOVA tests using one way Anova tool (significance level=0.05) using Origin Pro v. 8 Software (OriginLab, USA).

Results

Figure 8A:
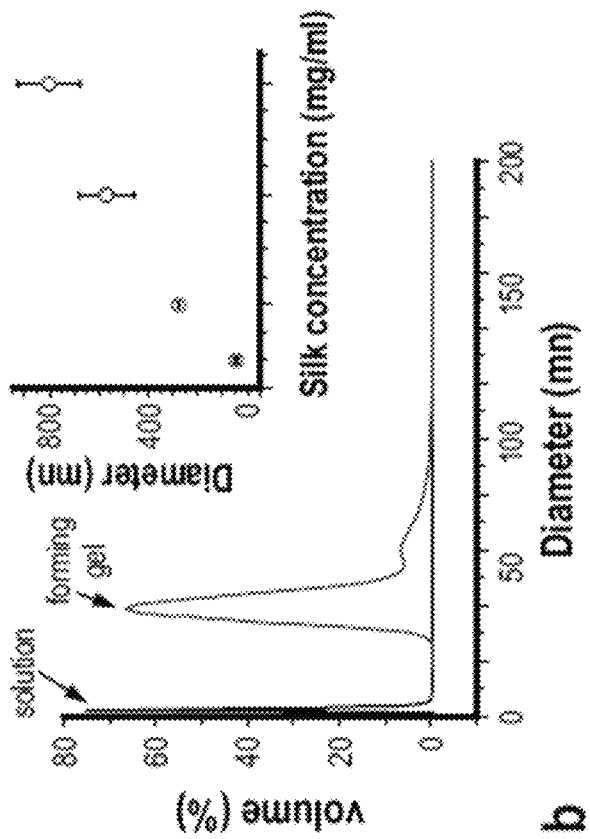
FIGS. 8A-8D show optical, morphological and chemical characterization of silk fibroin-based hydrogels.
Figure 8B:
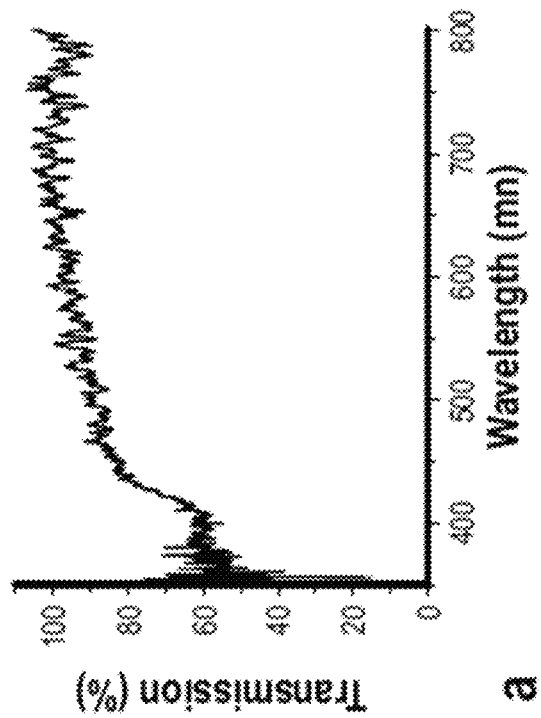

Dynamic light scattering (DLS) measurements showed that mixing silk fibroin solution at concentrations ranging from 10 to 15 mg/ml with various polar organic solvents (i.e. acetone, ethanol, methanol, isopropanol) drives the assembly of silk micelles into submicron-sized particles (<100 nm) (FIG. 8(b)), which is a unique feature when compared to previously reported larger fibroin particles (in the 100-5, 000 nm range) obtained through the exposure of silk solutions at higher concentrations (>20 mg/ml) to alcohols and ketones. These data are also consistent with a previously reported study, where silk fibroin precipitation in an acetone reservoir allowed for the formation of uniform silk nanoparticles (98 nm diameter, polydispersity index 0.109), which were used as a controlled drug release system for chemotherapeutics. (See F. P. Seib et al., 2 Adv. Healthc. Mater., 1606-11 (2013) the entire contents of which are herein incorporated by reference).

Figure 12:
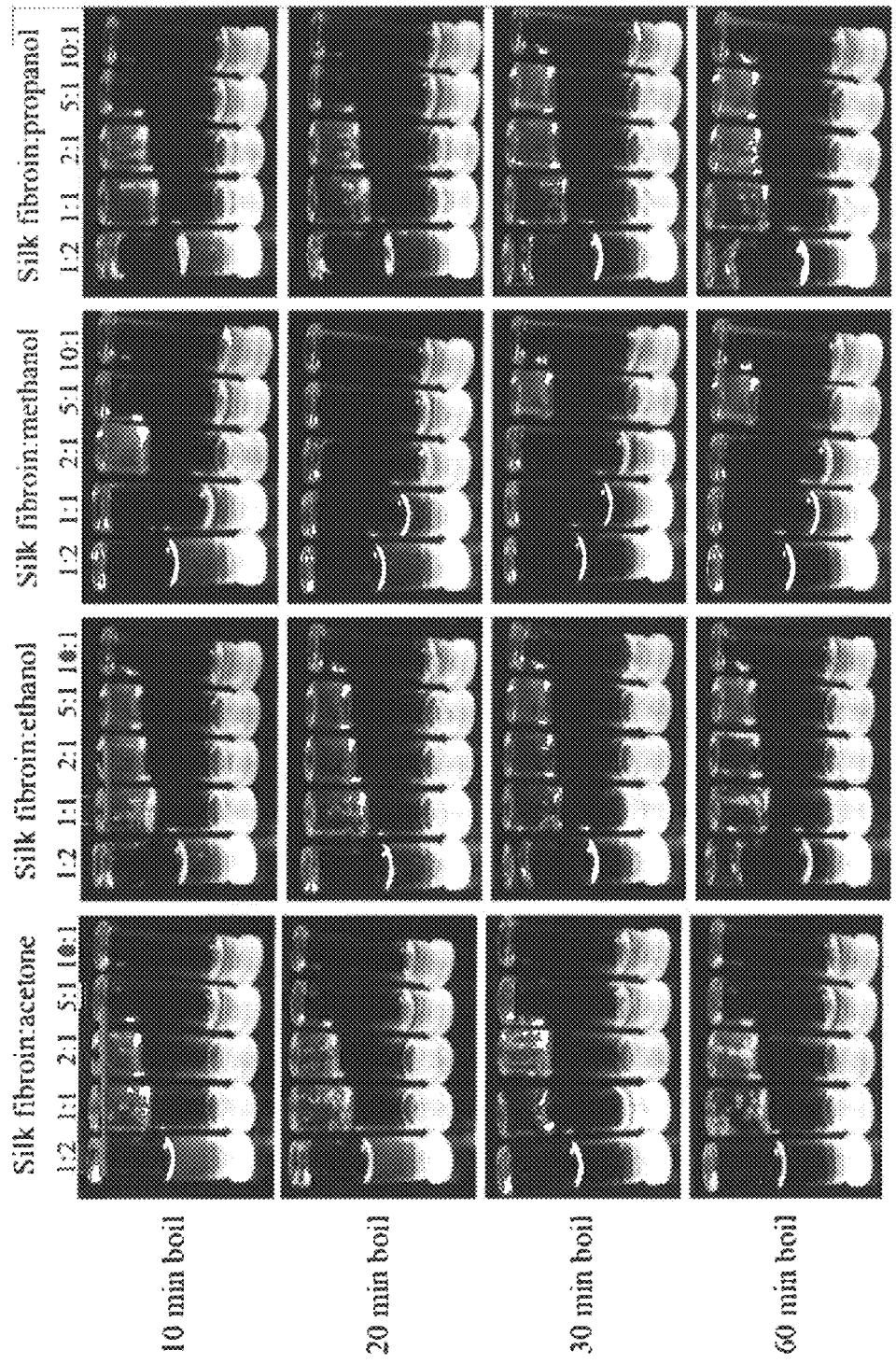
FIG. 12 shows effects of polar organic solvent treatments, silk fibroin boiling time at the point of sericin removal and silk fibroin:solvent ratios on gel formation. Original concentration of silk fibroin in water solution was 10 mg/ml and pictures were taken after one hour of treatment with organic solvents. The images depict the range of nanogelation and silk processing parameters (polar organic solvent treatments, silk fibroin:solvent ratios, silk fibroin boiling time at the point of sericin removal) within which nanogelation can be achieved.
Figure 13:
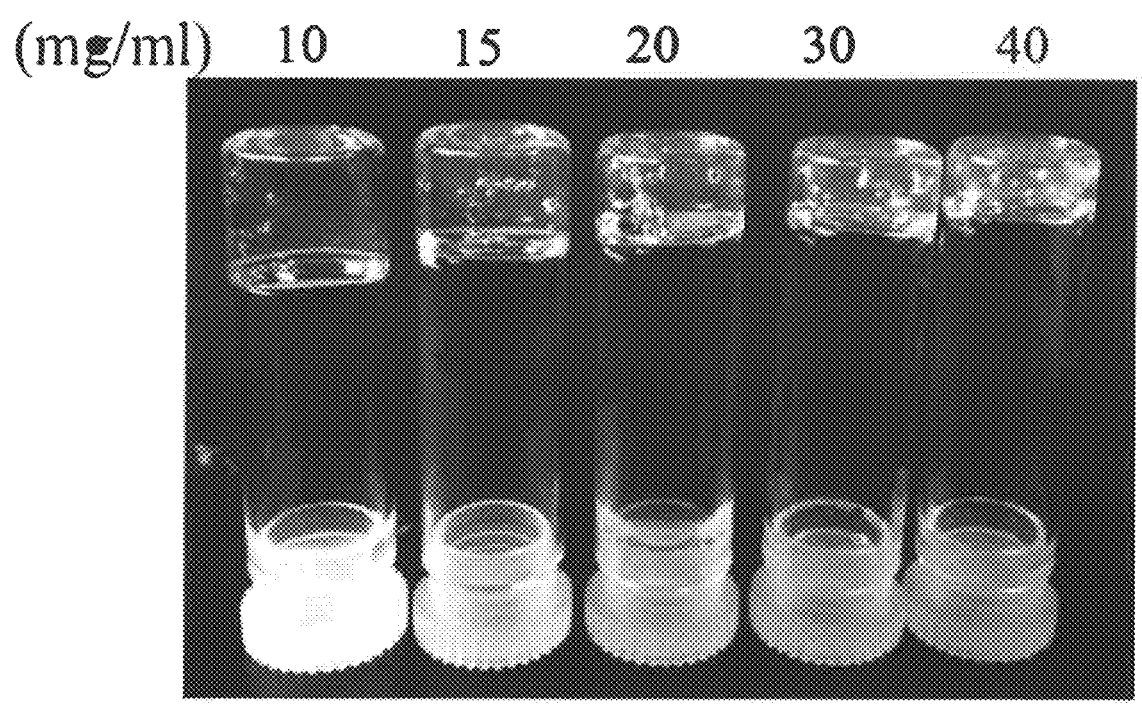
FIG. 13 shows gelation of silk fibroin in acetone at increasing silk fibroin concentrations. A concentration-dependent increase in light scattering was visible. The volume of silk fibroin solution was maintained constant throughout the experiment. Silk fibroin nanogelation was not achieved outside the indicated silk solution concentrations.
Figure 14:
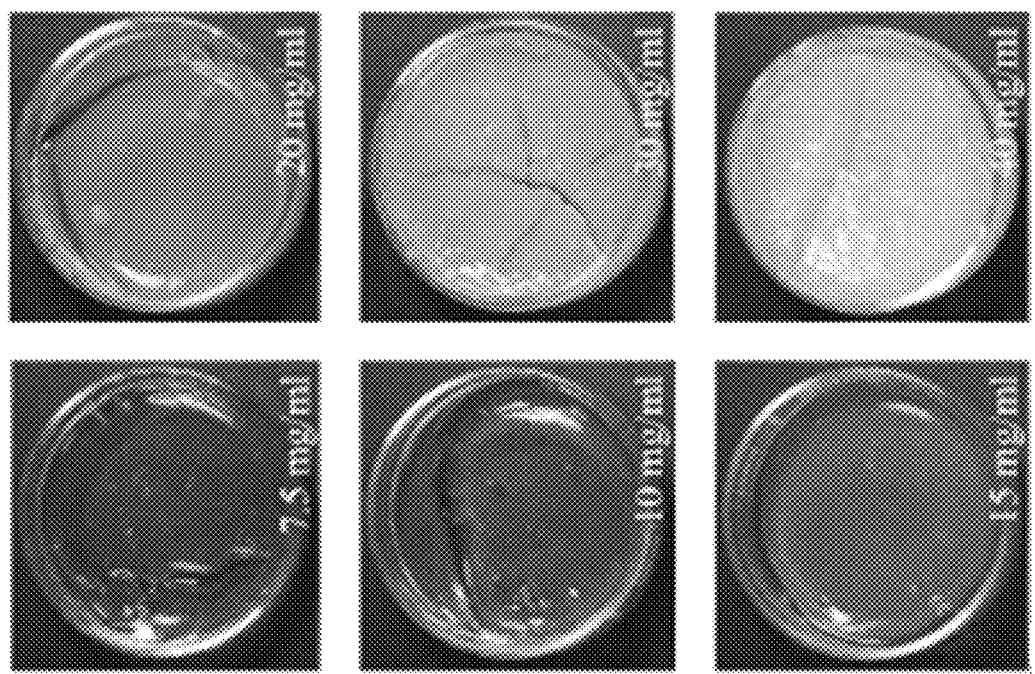
FIGS. 14A-14C show an effect of silk fibroin concentration and EDTA exposure time on nanogelation of silk fibroin-based hydrogels.
Figure 14B:
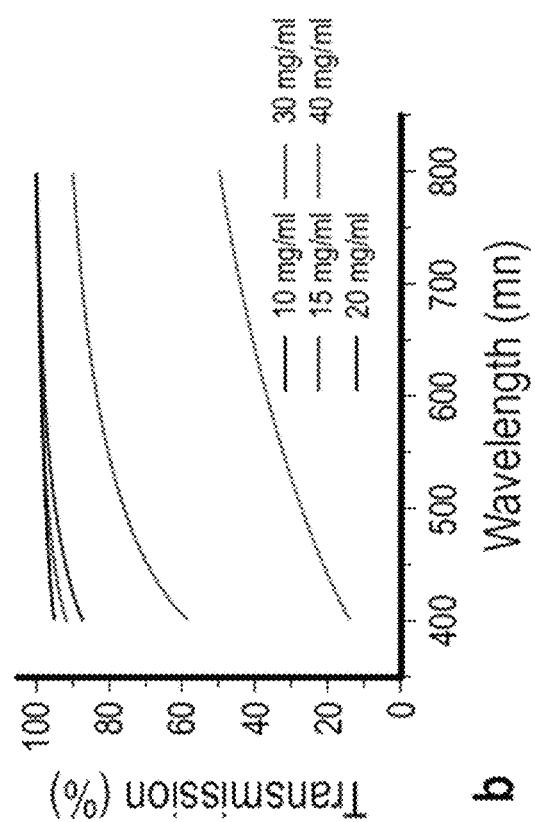

By leveraging the sol-gel transition, we developed an easy, fast and robust method to form nanoparticle-based silk hydrogels by mixing two parts of silk fibroin solution (average molecular weight of 100 kDa, 10 mg/ml) with one part of acetone, where the choice of organic solvent, silk fibroin solution parameters and the relative concentration of silk fibroin to organic solvent were selected to maximize gel integrity and transparency (FIG. 12, FIG. 13, FIG. 14(a)). Acetone was successfully removed during processing (FIG. 11(c)), and gelation in acetone provided enhanced transparency when compared to alcohols (FIG. 12).

In addition, silk fibroin concentration dictated the dimension of the silk particles within the forming hydrogel, and only silk solutions ≤15 mg/ml allowed to control silk fibroin particle diameter under 200 nm, resulting in optically clear hydrogels (FIG. 8(b), FIG. 13). By modulating silk fibroin molecular weight (MW) at the point of sericin removal from the raw fiber, silk fibroin solutions with an average MW of 100 kDa (corresponding to 30 minutes boiling time, (see L. S. Wray, et al., 99 J. Biomed. Mater. Res. B. Appl. Biomater., 89-101 (2011) the entire contents of which are herein incorporated by reference) provided the best trade-off between gel formation and transparency (FIG. 12).

Figure 8C:
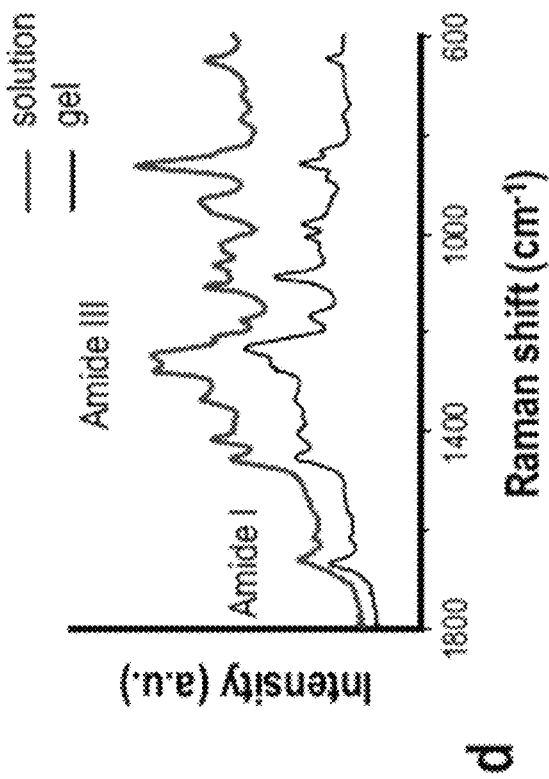
Figure 8D:
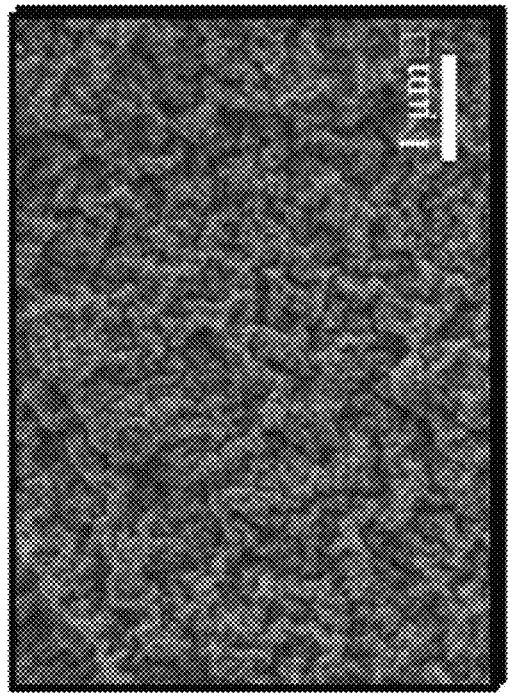
Figure 14C:
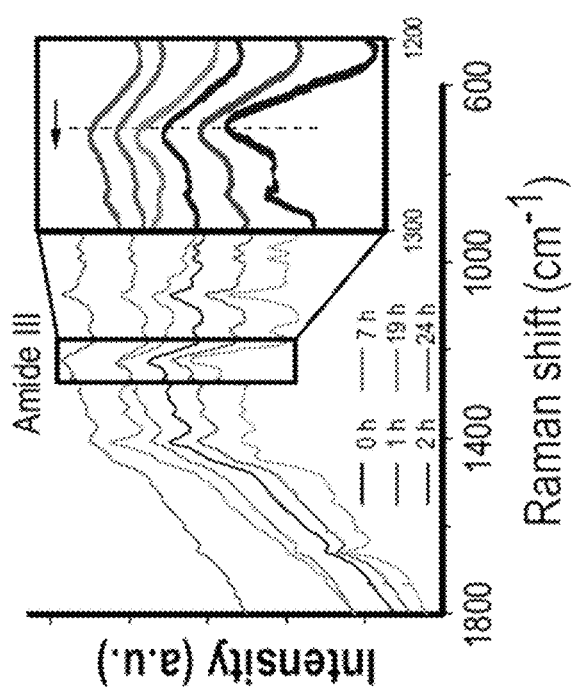
Figure 15:
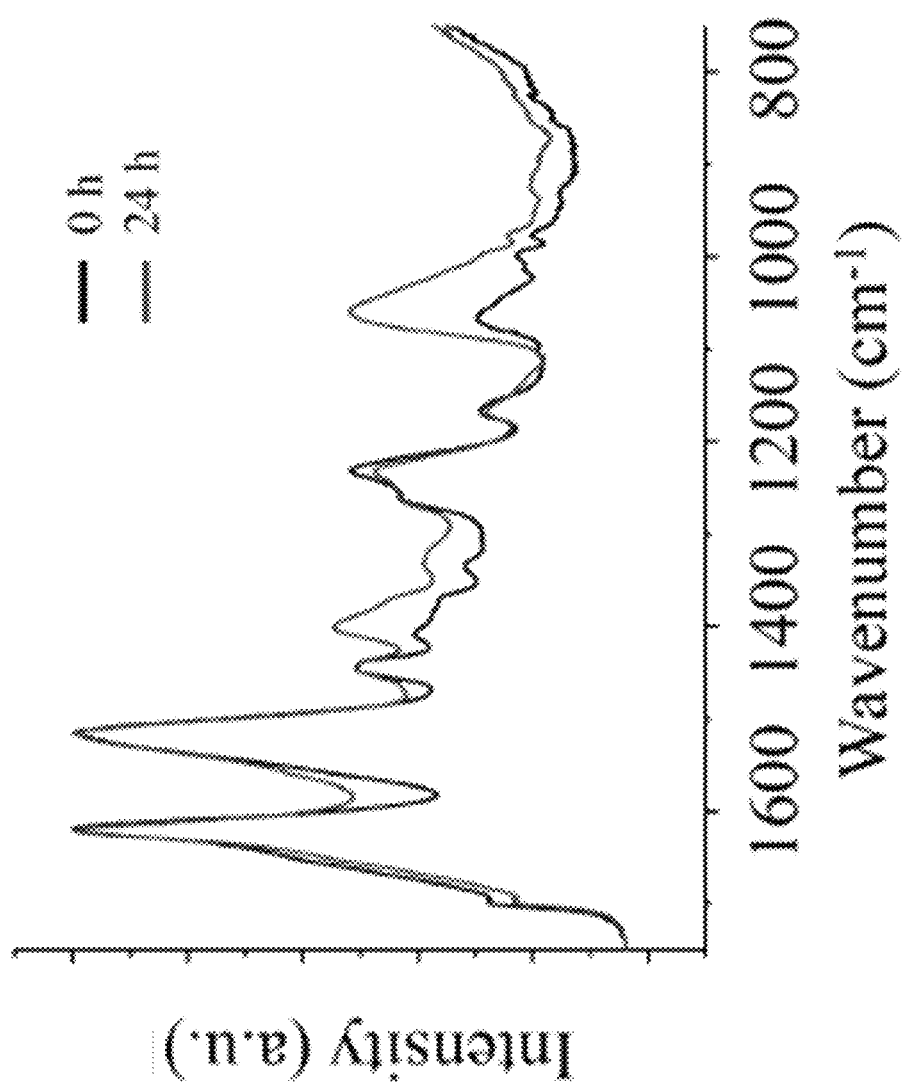
FIG. 15 shows an ATR-FTIR spectra of EDTA exposure time on ketonic gelation of silk fibroin-based hydrogels. Gels were conditioned in 20 mM EDTA solution for 0 h and 24 h before being rinsed in water. Crystallinity index (ratio of the absorbance at 1260/1230 $cm^{-1}$) of the samples increased from 0.83 to 0.92 upon treatment in EDTA.

The nanomorphology of transparent silk hydrogels was also evident by scanning electron microscopy, which depicted the assembly of silk fibroin in materials with morphological features less than 100 nm (FIG. 8(c)). The significance of material nanotopography has been previously demonstrated for stem cell differentiation (see M. J. Dalby, et al., 6 Nat. Mater., 997-1003 (2007) the entire contents of which are herein incorporated by reference), cell adhesion (see T. J. Webster, et al., 20 Biomaterials, 1221-7 (1999) the entire contents of which ar herein incorporated by reference), and metabolic activity (see T. J. Webster, et al., 21 Biomaterials, 1803-10 (2000) the entire contents of which are herein incorporated by reference) and the fabrication of nanostructured silk fibroin-based hydrogels through nanogelation may be useful to probe biological activity.

μRaman measurements corroborated the amorphous to crystalline conformational change of silk fibroin during the sol-gel transition, as the Amide I and 111 scattering peaks of the protein shifted upon gelation from wavenumbers attributed to the amorphous silk (1661 cm$^{-1}$ for Amide I, 1251 and 1276 cm$^{-1}$ for Amide III) to β-sheet features (1669 and 1230 cm for Amide I and 111, respectively) (FIG. 8(d)). (See P. Monti, et al., 29 J. Raman Spectrosc., 297-304 (1998) and P. Monti, et al., 32 J. Raman Spectrosc., 103-107 (2001) the entire contents of which are herein incorporated by reference). The control of crystallinity enables the modulation of the protein biodegradation in vivo and in vitrofom hours to months and years. (See E. M. Pritchard, et al., 13 Macromol. Biosci., 311-20 (2013). R. C. Preda, et al., 996 Methods Mol. Biol., 19-41 (2013), Y. Cao, et al., 10 Int. J. Mol. Sci., 1514-24 (2009), T. Arai, et al., 91 J. Appl. Polym. Sci., 2383-2390 (2004), and Y. Wang, et al., 29 Biomaterials, 3415-28 (2008) the entire contents of which are herein incorporated by reference). It is in fact hypothesized that enhanced crystallinity corresponds to a more packed, hydrophobic, structure that decreases accessibility by metalloproteinases (e.g. MMP1, MMP3, MMP9, MMP13) and other proteolytic enzymes (e.g. chymotrypsin, trypsin) to cleavage sites in the protein (unpublished data). Concurrently, the modulation of crystallinity allows for the regulation of mechanical properties of the material as the expulsion of water from the protein structure together with the formation of inter-molecular hydrogen bonds result in enhanced elastic modulus and yield strength. (See X. Hu, et al., 12 Biomacromolecules, 1686-96 (2011) the entire contents of which are herein incorporated by reference). To exploit the unique regulation of silk fibroin-based materials properties with hydrogels, it is common to modulate β-sheet formation by exposing silk fibroin-based hydrogels to alcohols (e.g. ethanol and methanol). (See D. N. Rockwood, et al., 6 Nat. Protoc., 1612-31 (2011) the entire contents of which are herein incorporated by reference). However, this type of treatment did not result in any significant impact effects on the conformation of the protein or on the mechanics of the hydrogels fabricated through nanogelation (data not shown), as the dehydration of the protein that drives the amorphous to crystalline transition was already achieved during the initial exposure to acetone during the sol-gel transition. Indeed, we pursued an unprecedented methodology to control fibroin crystallinity upon gel formation, which was predicated on the presence of salt bridges formed by metal ions inherently present in the silk fibroin structure and that perturb intermolecular bonding between silk fibroin nanoparticles. (See L. Zhou, et al., 109 J. Phys. Chem. B, 16937-45 (2005) and A. S. Lammel, et al., 31 Biomaterials, 4583-4591 (2010) the entire contents of which are herein incorporated by reference). We hypothesized that the exposure of silk fibroin-based hydrogels to solutions of aninopolycarboxylic acid, such as EDTA, would chelate the metal ions involved in the formation of salt-bridges, resulting in enhanced intermolecular bonding between the nanoparticles. EDTA has in fact a strong tendency to form stable complexes with metal ions and in particular with four of the six major metallic ions (Na$^+$, K$^+$, Mg$^{2+}$, Ca$^{2+}$, Cu$^{2+}$, and Zn$^{2+}$) in the secretory pathway in B. mori. (See L. Zhou, et al., 109 J. Phys. Chem. B, 16937-45 (2005) the entire contents of which are herein incorporated by reference). To test this hypothesis, silk fibroin-based hydrogels were exposed to 20 mM EDTA solution up to 24 hours and the changes in protein secondary and tertiary structures were determined by μRaman and ATR-FTIR spectroscopy. The analysis of the protein μRaman scattering in the Amide III region (1300-1200 cm$^{-1}$) showed a time-dependent blue shift of the fibroin crystalline Amide III scattering peak from 1230 cm$^{-1}$ to higher wavenumbers (FIG. 14(c)). Additionally, ATR-FTIR analysis of silk hydrogels before and after treatment in EDTA showed an increase in the crystallinity index of the protein (from 0.83 to 0.92, calculated as the 12601230 cm$^{-1}$ absorbance ratio) (see G. Freddi, et al., 24 Int. J. Biol. Macromol., 251-263 (1999) the entire contents of which are herein incorporated by reference), indicating an increase in the beta sheet content of the protein upon exposure to the aminopolycarboxylic acid (FIG. 15).

Figures 9A, 9B:
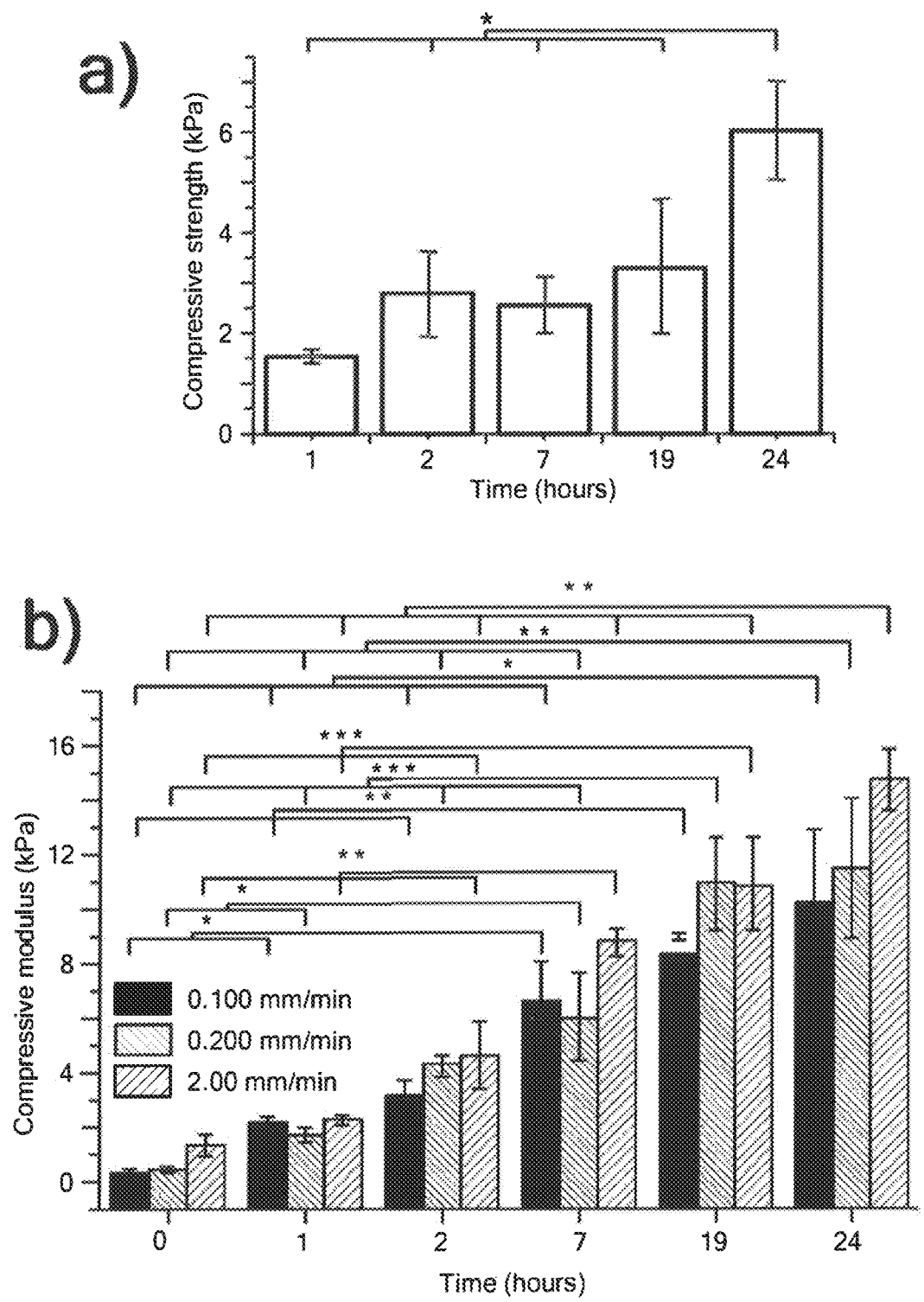
FIGS. 9A-9E show mechanical characterization of silk fibroin-based hydrogels.
Figures 9C, 9D, 9E:
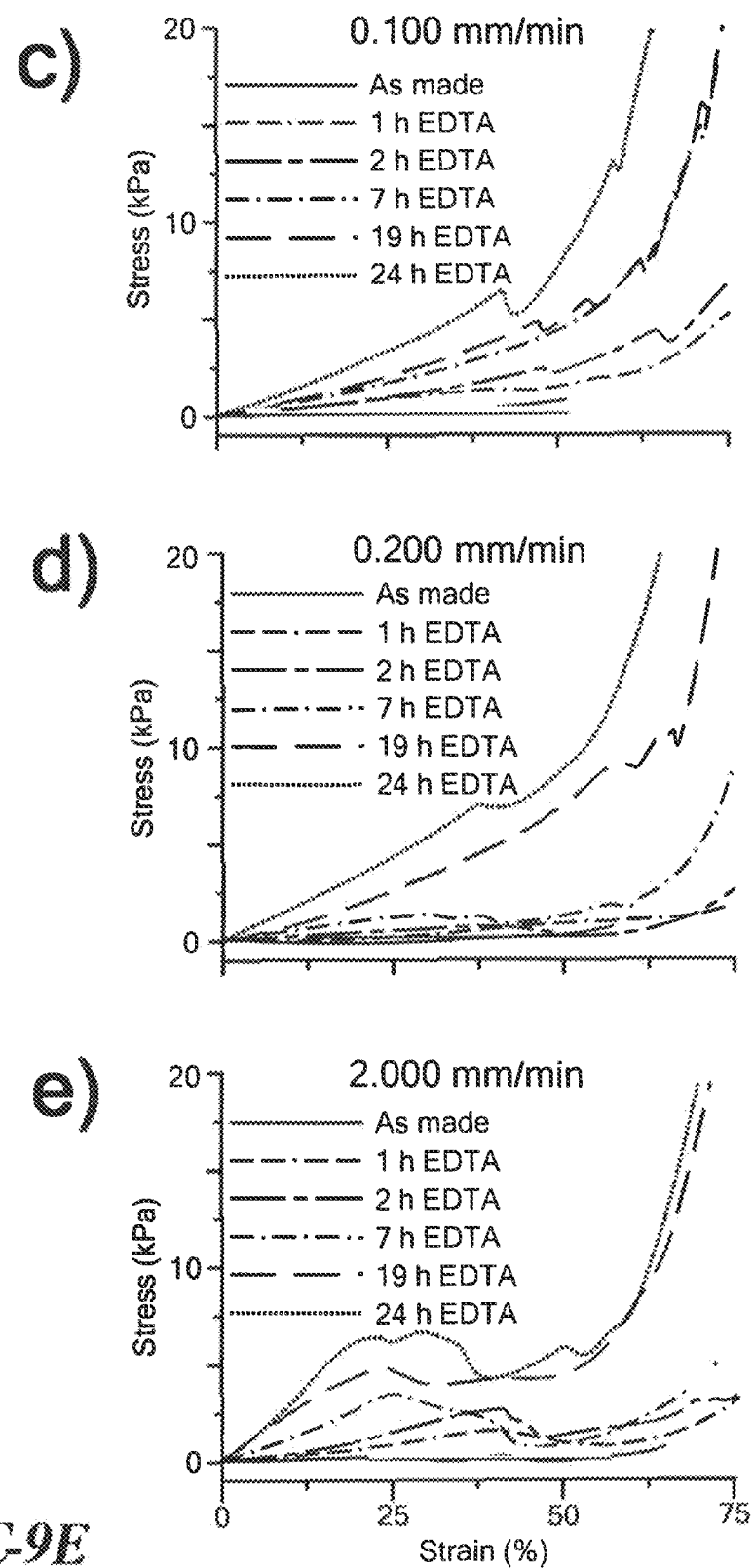

Compressive tests were carried out to evaluate the effect of the EDTA treatment on the mechanical properties of the hydrogels. FIG. 9 illustrates representative stress-strain curves at different crosshead speeds for increasing conditioning times in EDTA. All samples showed the densification behavior typical of soft material, where low compressive stress generates high material deformation. The typical viscoelastic behavior of silk hydrogels was also depicted, as increased crosshead speeds corresponded to increased stiffness. Silk fibroin-based hydrogels exposed to EDTA solution showed a time-dependent enhancement of mechanical properties; both compressive strength (FIG. 9(a)) and compressive modulus (FIG. 9(b)) increased. In particular, by controlling the exposure time to EDTA it was possible to regulate the compressive modulus of the hydrogels within a range spanning two orders of magnitude (from 0.4±0.183 to 11.5±2.6 kPa), which correspond to the stiffness of many body tissues ranging from the brain to the muscle. (See D. E. Discher, et al., 310 Science, 1139-43 (2005), A. J. Engler, et al., 126 Cell, 677-89 (2006), D. E. Discher, et al., 324 Science, 1673-7 (2009) the entire contents of which are herein incorporated by reference). Indeed, EDTA treatment of silk fibroin-based hydrogels not only allows for the modulation of the degree of crystallinity of the protein, which has been previously reported to control material biodegradation, but also to regulate the hydrogel mechanical properties, which impacts cell differentiation and overall cell behavior.

Figures 16A, 16B, 16C:
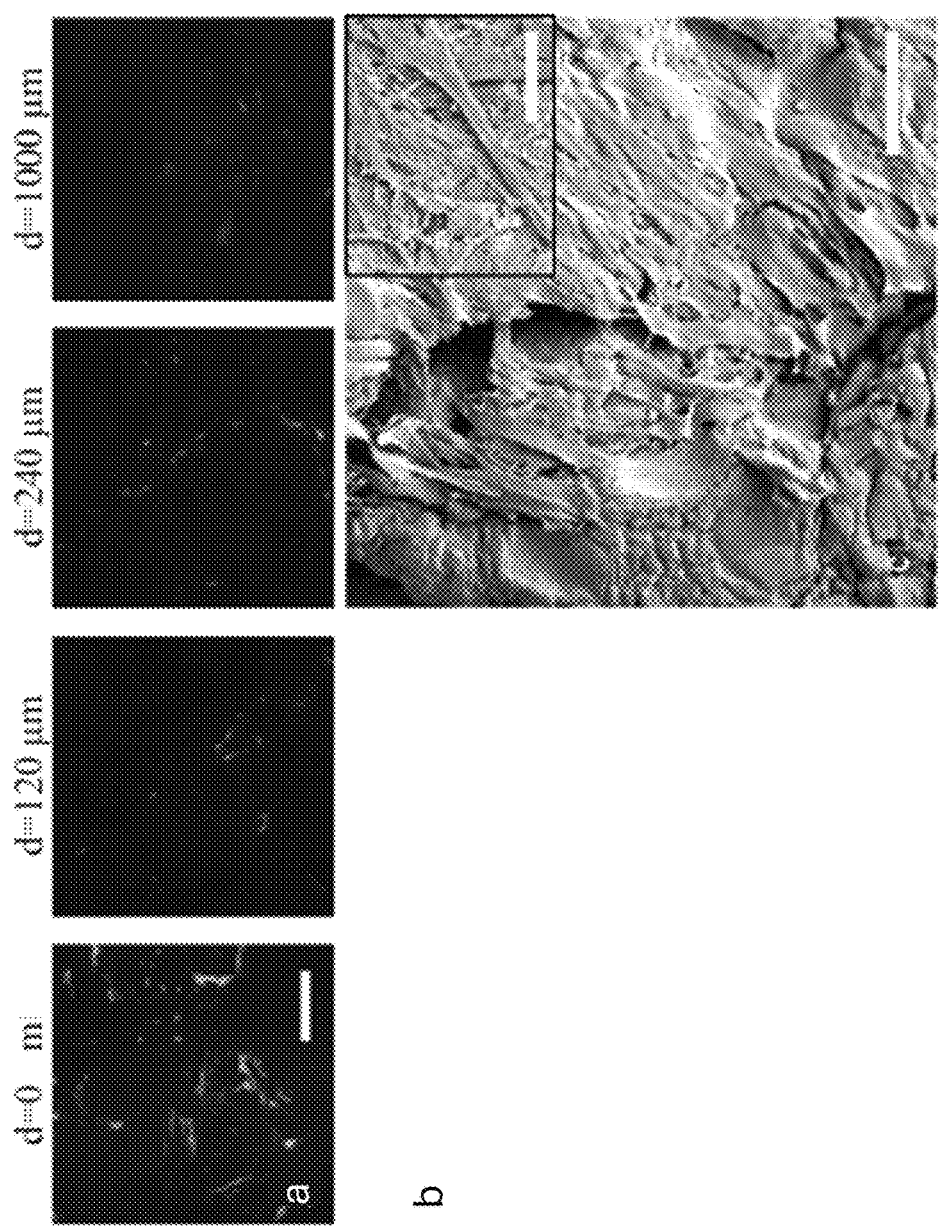
FIGS. 16A-16C show cytocompatibility of silk fibroin-based hydrogels obtained through nanogelation. Human dermal fibroblasts (HDFa) were cultured on silk fibroin-based hydrogels.
Figures 17A, 17B, 17C, 17D, 17E:
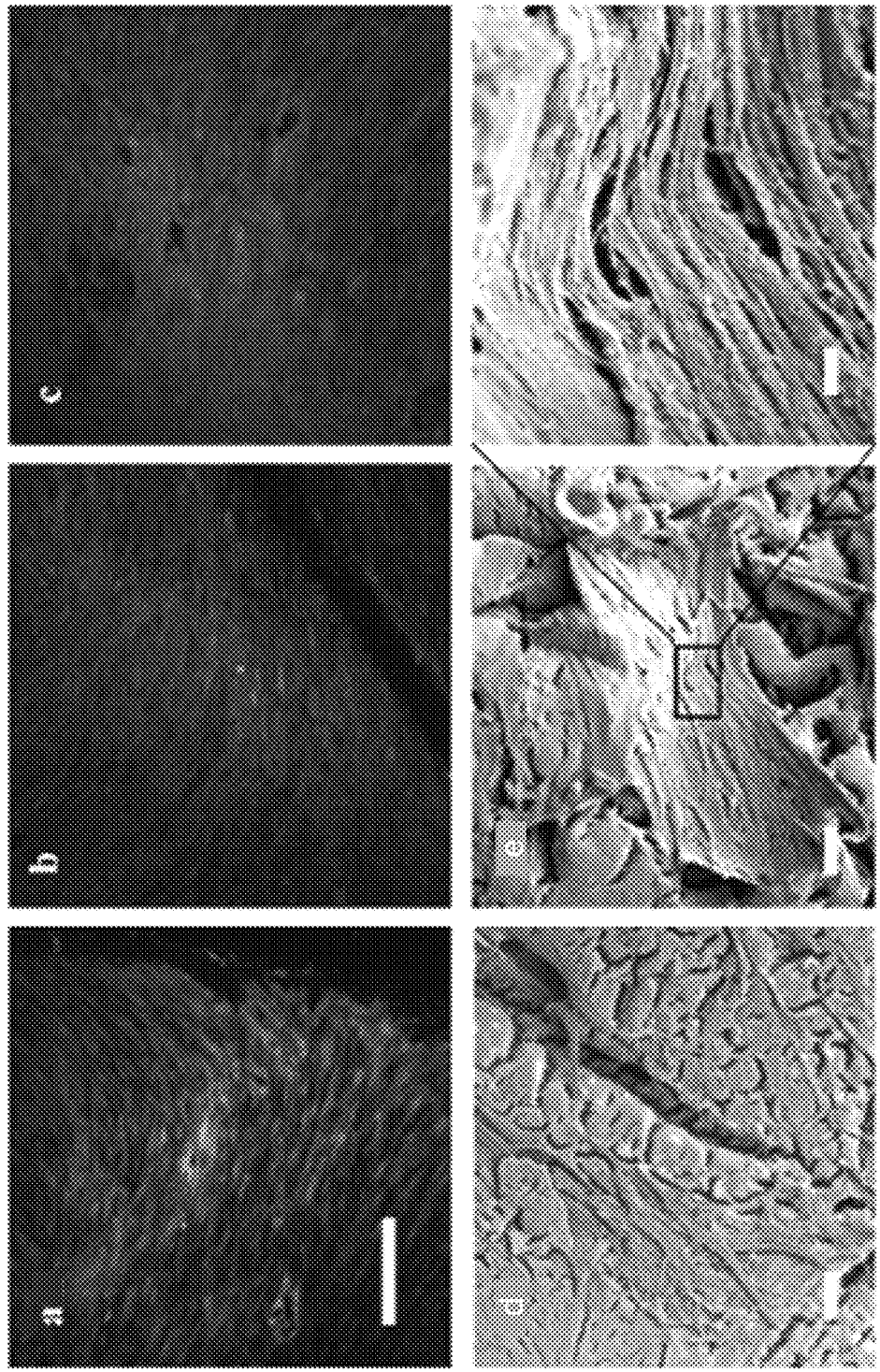
FIGS. 17A-17E show cytocompatibility of silk fibroin-based hydrogels obtained through nanogelation. Human dermal fibroblast (HDFa) were cultured on silk fibroin-based hydrogels

As a preliminary evaluation of biocompatibility, human dermal fibroblasts were cultured up to 28 days on silk fibroin-based hydrogels obtained with nanogelation and treated with EDTA for 24 hours. Confocal laser scanning microscopy images were taken of the dermal fibroblasts at day 7, 14 and 28 after staining with calcein-AM fluorescein and EtBr deoxyribonucleic acid binding (Live/Dead® (assay) (FIG. 16-FIG. 17). At day 7 (FIG. 16(a)), cells were viable (green) and attached to the surface of the hydrogel with negligible appearance of dead cells (red). Confocal imaging within the scaffolds allowed the visualization of living cells 1 mm into the gels, showing that the human dermal fibroblasts penetrated the hydrogel material and remained viable. In addition, SEM analysis of the cell-seeded hydrogels at day 7 showed deposition of extracellular matrix with a nanofibrillar structure, which can be associated to the formation of type I collagen from a fibroblastic cell-line. Prolonged culture times (days 14 and 28) of human fibroblasts on the silk fibroin-based hydrogels showed cell alignment and increased production of fibrillar nanostructures in the extracellular space (FIG. 16 and FIG. 17).

Figure 10A:
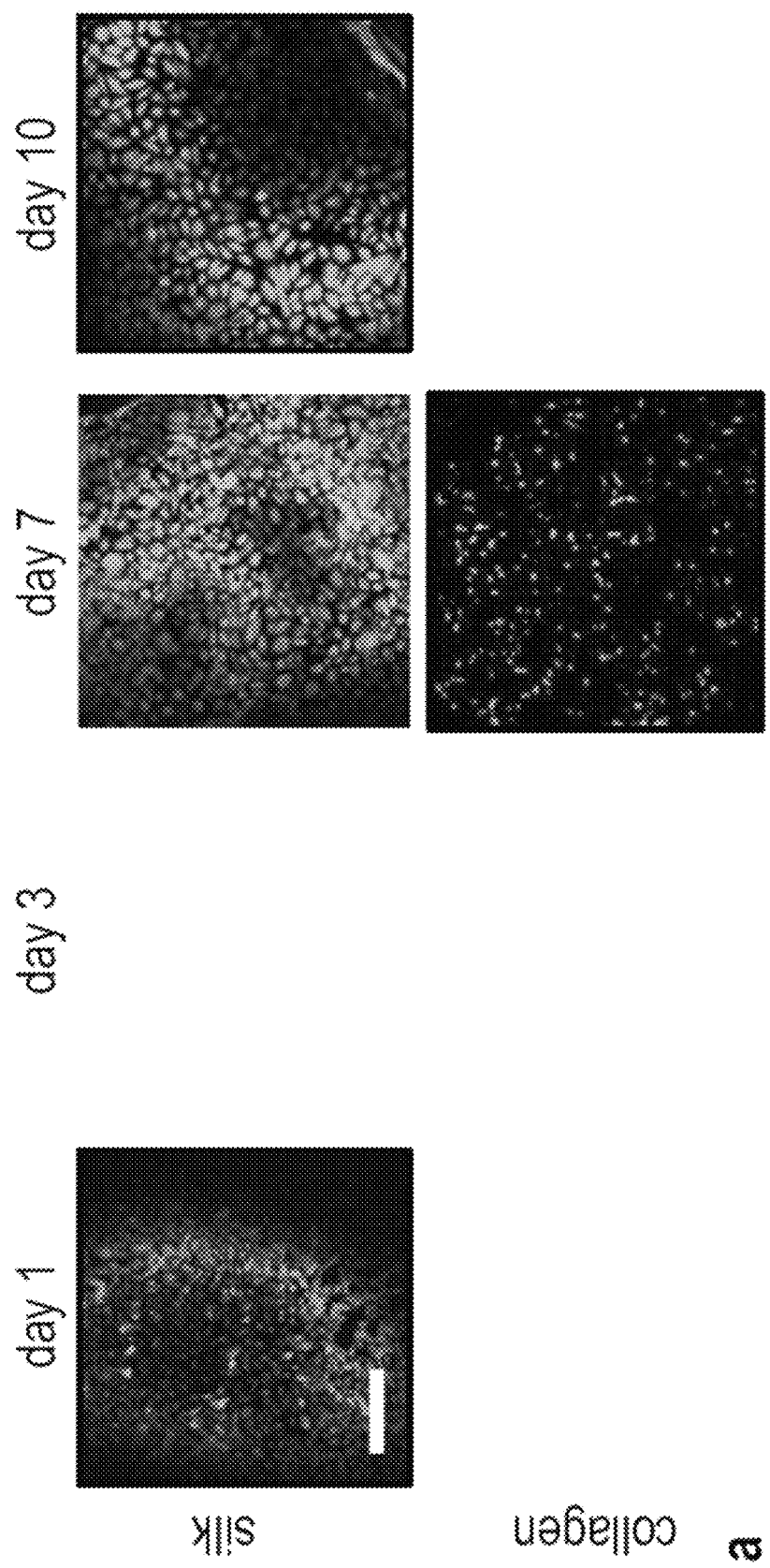
Figure 18:
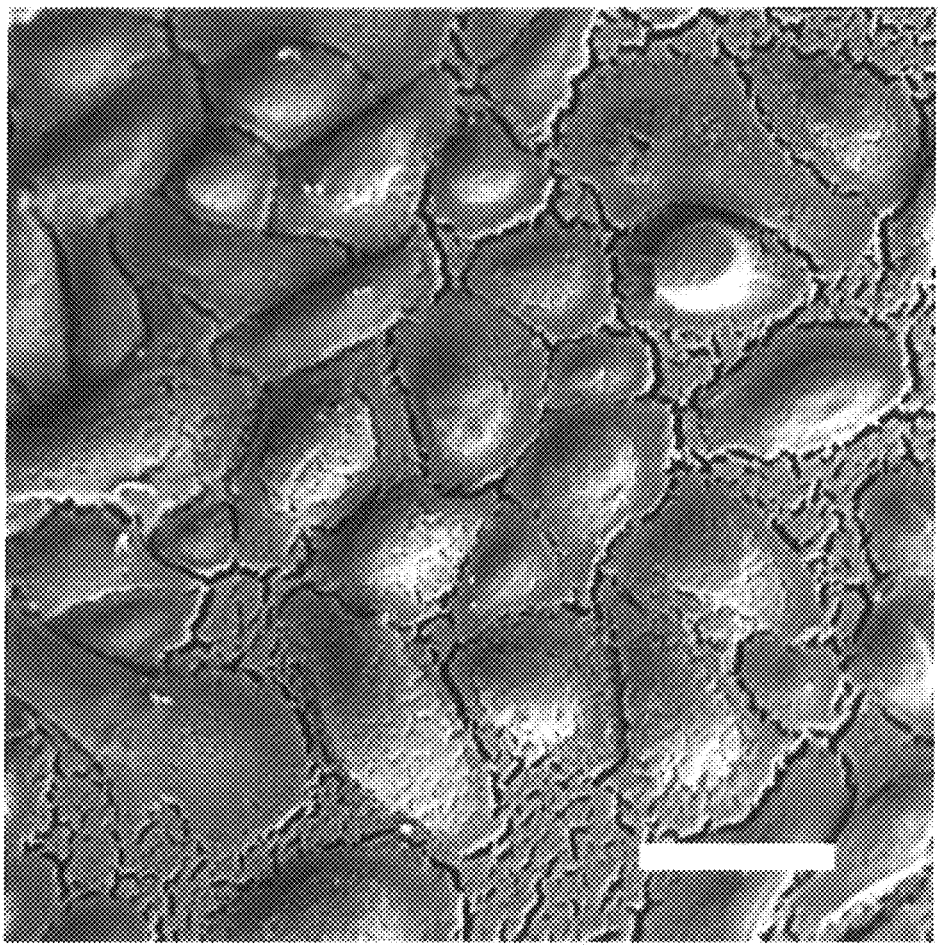
FIG. 18 shows an SEM micrograph of epithelial cornea cells cultured on the silk hydrogel at day 7 in culture. Scale bar is 40 μm.

Optically clear hydrogels can find use in regenerative medicine for transparent tissue scaffolds. As a proof of principle, silk fibroin-based hydrogels were seeded with human cornea epithelial cells (HCECs) to evaluate potential use as cornea-equivalent materials for epithelium regeneration. Type I collagen was chosen as positive control material, due to the material track record in the engineering of cornea with studies in human clinical phase (FIG. 10). (See A. Shah, et al., 63 Pediatr. Res., 535-44 (2008), P. Fagerholm, et al., 2 Science Transl Med. 46, 46-61 (2010), P. Fagerholm, et al., 35 Biomaterials, 2420-2427 (2014), X. Duan, et al., 27 Biomaterials, 4608-4617 (2006), and H. J. Levis, et al., 31 Biomaterials, 7726-7737 (2010) the entire contents of which are herein incorporated by reference). A combination of confocal laser microscopy and live/dead@ assay on HCEC-seeded silk fibroin-based hydrogels showed cell viability and proliferation over 10 days, with no appreciable difference when compared to collagen hydrogels. HCECs cultured on silk fibroin-based hydrogels also formed a visible epithelium at day 7 (FIG. 18). In addition, metabolic activity of HCECs seeded on silk fibroin and collagen hydrogels was measured as a function of culture time at days 1, 3, 7, and 10 using reduction of AlamarBlue™. The HCECs cultured on the silk fibroin-based hydrogels showed a similar (days 1, 3, 10, p>0.05) or increased (day 7, p<0.05) metabolic activity, when compared to HCECs cultured on collagen hydrogel counterparts. Optical transmission measurements of HCEC-seeded silk fibroin-based hydrogels at day 10 showed no appreciable difference to acellular counterparts, indicating that the hydrogels preserve transparency even with the formation of an epithelium (FIG. 10(c)) in contrast to similar measurements taken on HCECs-seeded collagen scaffold, which showed decrease in transparency of collagen hydrogels.

OTHER EMBODIMENTS AND EQUIVALENTS

While the present disclosure has explicitly discussed certain particular embodiments and examples of the present disclosure, those skilled in the art will appreciate that the invention is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

What is claimed is:

1. A composition comprising:
a plurality of crystalized silk fibroin spheres, wherein the crystalized silk fibroin spheres have a diameter between about 10 nm and about 150 nm,
the plurality of crystalized silk fibroin spheres arranged together to form a freestanding hydrogel structure having at least 60% optical transmittance in the visible spectrum.

2. The composition of claim 1, the freestanding hydrogel structure having at least 95% transmittance in the visible spectrum.

3. The composition of claim 1, the freestanding hydrogel structure having a compressive modulus between about 2 kPa and about 20 kPa when measured with a crosshead speed of about 2.0 mm/hr.

4. The composition of claim 1, wherein the silk fibroin within the silk fibroin spheres is crosslinked.

5. The composition of claim 4, wherein the silk fibroin is crosslinked with a crosslinking agent.

6. The composition of claim 5, wherein the crosslinking agent is an amine-to-amine crosslinker, amine-to-sulfhydryl crosslinker, carboxyl-to-amine crosslinker, photoreactive crosslinker, sulfhydryl-to-carbohydrate crosslinker, sulfhydryl-to-hydroxyl crosslinker, sulfhydryl-to-sulfhydryl crosslinker, or any combination thereof.

7. The composition of claim 5, wherein the crosslinking agent is EDTA.

8. A composition comprising:
nanosized crystalline particles comprising silk fibroin polypeptides having an average molecular weight falling within the range of about 3.5 kDa to about 120 kDa,
the nanosized crystalline particles having a diameter between about 10 nm and about 150 nm, and
the nanosized crystalline particles arranged together to form a freestanding hydrogel structure having at least 60% optical transmittance in the visible spectrum.

9. The composition of claim 8, the silk fibroin polypeptides having an average molecular weight falling within the range of about 25 kDa to about 120 kDa.

10. The composition of claim 8, the silk fibroin polypeptides having an average molecular weight falling within the range of about 75 kDa to about 120 kDa.

11. The composition of claim 8, wherein the freestanding hydrogel structure has at least one dimension that is at least 10 micrometers.

12. The composition of claim 8, the freestanding hydrogel structure having a compressive modulus between about 2 kPa and about 20 kPa when measured with a crosshead speed of about 2.0 mm/hr.

13. The composition of claim 8, the freestanding hydrogel structure comprising a predetermined microstructure fabricated therein.

14. The composition of claim 13, wherein the predetermined microstructure is a void.

15. A composition comprising:
a plurality of silk fibroin nanoparticles having a diameter between about 10 nm and about 150 nm,
the plurality of silk fibroin nanoparticles arranged together to form a freestanding hydrogel structure.

16. The composition of claim 15, wherein the plurality of silk fibroin nanoparticles are crosslinked by an amine-to-amine crosslinker, amine-to-sulfhydryl crosslinker, carboxyl-to-amine crosslinker, photoreactive crosslinker, sulfhydryl-to-carbohydrate crosslinker, sulfhydryl-to-hydroxyl crosslinker, sulfhydryl-to-sulfhydryl crosslinker, or any combination thereof.

17. The composition of claim 15, the plurality of silk fibroin nanoparticles having a diameter between about 50 nm and about 150 nm.

18. The composition of claim 15, the plurality of silk fibroin nanoparticles having a diameter between about 80 nm and about 120 nm.

19. The composition of claim 15, the freestanding hydrogel structure having at least 60% transmittance in the visible spectrum.

20. The composition of claim 15, the plurality of silk fibroin nanoparticles having a porosity between about 0% and about 50%.

* * * * *